(12) United States Patent
Wilson et al.

(10) Patent No.: US 10,080,878 B2
(45) Date of Patent: Sep. 25, 2018

(54) CATHETER WITH MULTIPLE ULTRASOUND RADIATING MEMBERS

(71) Applicant: EKOS CORPORATION, Bothell, WA (US)

(72) Inventors: Richard R. Wilson, Seattle, WA (US); Robert L. Wilcox, Bothell, WA (US); Curtis Genstler, Snohomish, WA (US); Tim Abrahamson, Seattle, WA (US); Wm. Gerrit Barrere, Lake Forest Park, WA (US); Amy Cohen, Seattle, WA (US); George Keilman, Seattle, WA (US); Leonard R. Oliver, Seattle, WA (US); Natalya Peskin, Redmond, WA (US)

(73) Assignee: EKOS CORPORATION, Bothell, WA (US)

( * ) Notice: Subject to any disclaimer, the term of this patent is extended or adjusted under 35 U.S.C. 154(b) by 0 days.

(21) Appl. No.: 15/207,371

(22) Filed: Jul. 11, 2016

(65) Prior Publication Data
US 2017/0007815 A1    Jan. 12, 2017

Related U.S. Application Data

(60) Continuation of application No. 14/196,225, filed on Mar. 4, 2014, now Pat. No. 9,415,242, which is a
(Continued)

(51) Int. Cl.
*A61M 37/00* (2006.01)
*A61B 17/22* (2006.01)
(Continued)

(52) U.S. Cl.
CPC ..... *A61M 37/0092* (2013.01); *A61B 17/2202* (2013.01); *A61M 25/0029* (2013.01);
(Continued)

(58) Field of Classification Search
CPC ................. A61M 37/0092; A61M 2025/0034–2025/004; A61M 25/0029;
(Continued)

(56) References Cited

U.S. PATENT DOCUMENTS 3,352,303 A    11/1967  Delaney
3,430,625 A     3/1969  McLeod, Jr.
(Continued)

FOREIGN PATENT DOCUMENTS

DE    40 05 743     8/1991
EP    0 529 675     3/1993
(Continued)

OTHER PUBLICATIONS

Chamsuddin et al., "Catheter-directed Thrombolysis with the Endowave System in the Treatment of Acute Massive Pulmonary Embolism: A Retrospective Multicenter Case Series," Journal of Vascular and Interventional Radiology, Mar. 2008, vol. 19, No. 3, pp. 372-376.
(Continued)

*Primary Examiner* — Nathan R Price
*Assistant Examiner* — Melissa A Snyder
(74) *Attorney, Agent, or Firm* — Knobbe, Martens, Olson & Bear LLP

(57) ABSTRACT

A method of delivery ultrasonic energy and a therapeutic compound to a treatment site and an ultrasonic catheter system are disclosed. The ultrasonic catheter system comprises a tubular body having a proximal end, a distal end and a treatment zone located between the distal end and the proximal end, a fluid delivery lumen, at least one ultrasound radiating element positioned in the treatment zone, wiring electrically coupled to the at least one ultrasound radiating element and extending through the tubular body and terminating at a connector, and a control system comprising external circuitry and an isolation pod that is configured to
(Continued)

be electrically connected to the connector, the isolation pod being positioned between the tubular body and the external system and comprising an isolation barrier and circuitry for driving the ultrasound radiating element.

11 Claims, 25 Drawing Sheets

Related U.S. Application Data continuation of application No. 13/431,798, filed on Mar. 27, 2012, now Pat. No. 8,696,612, which is a continuation of application No. 12/762,254, filed on Apr. 16, 2010, now Pat. No. 8,167,831, which is a division of application No. 11/643,471, filed on Dec. 21, 2006, now Pat. No. 7,727,178, which is a division of application No. 10/309,388, filed on Dec. 3, 2002, now Pat. No. 7,220,239.

(60) Provisional application No. 60/394,093, filed on Jul. 3, 2002, provisional application No. 60/336,744, filed on Dec. 3, 2001, provisional application No. 60/336,630, filed on Dec. 3, 2001.

(51) Int. Cl.
*A61M 25/00* (2006.01)
*A61N 7/00* (2006.01)

(52) U.S. Cl.
CPC .......... *A61M 25/0032* (2013.01); *A61N 7/00* (2013.01); *A61B 2017/22084* (2013.01); *A61B 2017/22088* (2013.01); *A61N 2007/0078* (2013.01)

(58) Field of Classification Search
CPC ... A61M 25/0032; A61B 17/2202; A61N 7/00
See application file for complete search history.

(56) References Cited

U.S. PATENT DOCUMENTS

| | | |
|---|---|---|
| 3,433,226 A | 3/1969 | Boyd |
| 3,565,062 A | 2/1971 | Kuris |
| 3,827,115 A | 8/1974 | Bom |
| 3,861,391 A | 1/1975 | Antonevich et al. |
| 3,941,122 A | 3/1976 | Jones |
| 3,976,987 A | 8/1976 | Anger |
| 4,040,414 A | 8/1977 | Suroff |
| 4,192,294 A | 3/1980 | Vasilevsky et al. |
| 4,309,989 A | 1/1982 | Fahim |
| 4,319,580 A | 3/1982 | Colley et al. |
| 4,354,502 A | 10/1982 | Colley et al. |
| 4,531,943 A | 7/1985 | Van Tassel |
| 4,549,533 A | 10/1985 | Cain et al. |
| 4,587,975 A | 5/1986 | Salo et al. |
| 4,682,596 A | 7/1987 | Bales et al. |
| 4,692,139 A | 9/1987 | Stiles |
| 4,709,698 A | 12/1987 | Johnston et al. |
| 4,750,902 A | 6/1988 | Wuchinich |
| 4,754,752 A | 7/1988 | Ginsburg et al. |
| 4,770,185 A | 9/1988 | Silverstein et al. |
| 4,808,153 A | 2/1989 | Parisi |
| 4,821,740 A | 4/1989 | Tachibana et al. |
| 4,841,977 A | 6/1989 | Griffith et al. |
| 4,870,953 A * | 10/1989 | DonMicheal .... A61B 17/22012 604/22 |
| 4,920,954 A | 5/1990 | Alliger |
| 4,921,478 A | 5/1990 | Solano et al. |
| 4,924,863 A | 5/1990 | Sterzer |
| 4,933,843 A | 6/1990 | Scheller et al. |
| 4,936,281 A | 6/1990 | Stasz |
| 4,948,587 A | 8/1990 | Kost et al. |
| 4,951,677 A | 8/1990 | Crowley |
| 4,953,565 A | 9/1990 | Tachibana et al. |
| 4,960,109 A | 10/1990 | Lele |
| 4,971,991 A | 11/1990 | Umemura et al. |
| 5,007,438 A | 4/1991 | Tachibana et al. |
| 5,021,044 A | 6/1991 | Sharkawy |
| 5,026,387 A * | 6/1991 | Thomas ........... A61B 17/32006 310/316.01 |
| 5,053,008 A | 10/1991 | Bajaj |
| 5,058,570 A | 10/1991 | Idemoto et al. |
| 5,059,851 A | 10/1991 | Corl |
| 5,069,664 A | 12/1991 | Guess |
| 5,076,276 A | 12/1991 | Sakurai et al. |
| 5,088,499 A | 2/1992 | Unger |
| 5,108,369 A | 4/1992 | Ganguly et al. |
| 5,129,883 A | 7/1992 | Black |
| 5,149,319 A | 9/1992 | Unger |
| 5,158,071 A | 10/1992 | Umemura et al. |
| 5,163,421 A | 11/1992 | Bernstein et al. |
| 5,163,436 A | 11/1992 | Saitoh et al. |
| 5,178,620 A | 1/1993 | Eggers et al. |
| 5,185,071 A | 2/1993 | Serwer et al. |
| 5,197,946 A | 3/1993 | Tachibana |
| 5,226,421 A | 7/1993 | Frisbie |
| 5,250,034 A | 10/1993 | Appling et al. |
| 5,261,291 A | 11/1993 | Schoch et al. |
| 5,267,954 A | 12/1993 | Nita |
| 5,267,985 A | 12/1993 | Shimada |
| 5,269,291 A | 12/1993 | Carter |
| 5,271,406 A | 12/1993 | Ganguly |
| 5,279,546 A * | 1/1994 | Mische ............ A61B 17/22012 604/101.03 |
| 5,282,785 A | 2/1994 | Shapland et al. |
| 5,286,254 A | 2/1994 | Shapland |
| 5,295,484 A | 3/1994 | Marcus et al. |
| 5,304,115 A | 4/1994 | Pflueger |
| 5,307,816 A | 5/1994 | Hashimoto |
| 5,312,328 A | 5/1994 | Nita et al. |
| 5,313,949 A | 5/1994 | Yock |
| 5,315,998 A | 5/1994 | Tachibana et al. |
| 5,318,014 A | 6/1994 | Carter |
| 5,323,769 A | 6/1994 | Bommannan |
| 5,326,342 A | 7/1994 | Pflueger |
| 5,327,891 A | 7/1994 | Rammler |
| 5,328,470 A | 7/1994 | Nabel |
| 5,342,292 A | 8/1994 | Nita et al. |
| 5,344,395 A | 9/1994 | Whalen et al. |
| 5,344,435 A | 9/1994 | Turner |
| 5,345,940 A | 9/1994 | Seward |
| 5,348,481 A | 9/1994 | Oritz |
| 5,351,693 A | 10/1994 | Taimisto |
| 5,353,798 A | 10/1994 | Sieben |
| 5,354,279 A | 10/1994 | Hofling |
| 5,362,309 A | 11/1994 | Carter |
| 5,363,853 A | 11/1994 | Lieber |
| 5,368,036 A | 11/1994 | Tanaka et al. |
| 5,368,557 A | 11/1994 | Nita |
| 5,368,558 A | 11/1994 | Nita |
| 5,370,675 A | 12/1994 | Edwards |
| 5,372,138 A | 12/1994 | Crowley et al. |
| 5,380,273 A | 1/1995 | Dubrul et al. |
| 5,385,148 A | 1/1995 | Lesh et al. |
| 5,390,678 A | 2/1995 | Gesswein |
| 5,397,293 A | 3/1995 | Alliger |
| 5,399,158 A | 3/1995 | Lauer et al. |
| 5,401,237 A | 3/1995 | Tachibana et al. |
| 5,405,322 A | 4/1995 | Lennox et al. |
| 5,421,338 A | 6/1995 | Crowley |
| 5,423,797 A | 6/1995 | Adrian et al. |
| 5,431,663 A | 7/1995 | Carter |
| 5,440,914 A | 8/1995 | Tachibana et al. |
| 5,445,155 A | 8/1995 | Sieben |
| 5,447,509 A | 9/1995 | Mills et al. |
| 5,447,510 A | 9/1995 | Jensen |
| 5,453,575 A | 9/1995 | O'Donell et al. |
| 5,456,259 A | 10/1995 | Barlow et al. |
| 5,458,568 A | 10/1995 | Racchini |
| 5,462,523 A | 10/1995 | Samson |
| 5,465,726 A | 11/1995 | Dickinson |

(56) References Cited

U.S. PATENT DOCUMENTS

| | | |
|---|---|---|
| 5,474,530 A | 12/1995 | Passafaro |
| 5,474,531 A | 12/1995 | Carter |
| 5,498,236 A | 3/1996 | Dubrul et al. |
| 5,498,238 A | 3/1996 | Shapland |
| 5,509,896 A | 4/1996 | Carter |
| 5,514,092 A | 5/1996 | Forman |
| 5,520,189 A | 5/1996 | Malinowski |
| 5,523,058 A | 6/1996 | Umemura |
| 5,533,986 A | 7/1996 | Mottola |
| 5,542,917 A | 8/1996 | Nita et al. |
| 5,542,935 A | 8/1996 | Unger et al. |
| 5,558,092 A | 9/1996 | Unger et al. |
| 5,560,362 A | 10/1996 | Sliwa, Jr. et al. |
| 5,569,197 A | 10/1996 | Helmus |
| 5,582,586 A | 12/1996 | Tachibana et al. |
| 5,588,432 A | 12/1996 | Crowley |
| 5,603,327 A | 2/1997 | Eberle |
| 5,603,694 A | 2/1997 | Brown |
| 5,606,974 A | 3/1997 | Castellano |
| 5,617,851 A | 4/1997 | Lipkovker |
| 5,618,275 A | 4/1997 | Bock |
| 5,620,409 A | 4/1997 | Gans et al. |
| 5,620,479 A | 4/1997 | Diederich |
| 5,624,382 A | 4/1997 | Oppelt |
| 5,628,728 A | 5/1997 | Tachibana et al. |
| 5,628,730 A | 5/1997 | Shapland |
| 5,630,837 A | 5/1997 | Crowley |
| 5,648,098 A | 7/1997 | Porter |
| 5,656,016 A | 8/1997 | Ogden |
| 5,660,180 A | 8/1997 | Malinowski |
| 5,660,909 A | 8/1997 | Tachibana et al. |
| 5,665,076 A | 9/1997 | Roth |
| 5,681,296 A | 10/1997 | Ishida |
| 5,695,460 A | 12/1997 | Siegel et al. |
| 5,697,897 A | 12/1997 | Buchholtz et al. |
| 5,713,831 A | 2/1998 | Olsson |
| 5,713,848 A | 2/1998 | Dubrul et al. |
| 5,720,710 A | 2/1998 | Tachibana et al. |
| 5,724,976 A | 3/1998 | Hirama et al. |
| 5,725,494 A | 3/1998 | Brisken |
| 5,728,062 A | 3/1998 | Brisken |
| 5,733,315 A | 3/1998 | Burdette et al. |
| 5,735,811 A | 4/1998 | Brisken |
| 5,752,930 A | 5/1998 | Baudino et al. |
| 5,772,632 A | 6/1998 | Forman |
| 5,775,338 A | 7/1998 | Hastings |
| 5,779,673 A | 7/1998 | Roth |
| 5,807,395 A | 9/1998 | Mulier et al. |
| 5,817,021 A | 10/1998 | Reichenberger |
| 5,823,962 A | 10/1998 | Lerch et al. |
| 5,827,203 A | 10/1998 | Nita |
| 5,827,313 A | 10/1998 | Ream |
| 5,834,880 A | 11/1998 | Lewandowski et al. |
| 5,836,896 A | 11/1998 | Rosenschein |
| 5,836,940 A | 11/1998 | Gregory |
| 5,840,031 A | 11/1998 | Crowley |
| 5,842,994 A | 12/1998 | Tenhoff et al. |
| 5,846,218 A | 12/1998 | Brisken et al. |
| 5,876,345 A | 3/1999 | Eaton et al. |
| 5,908,445 A | 6/1999 | Whayne et al. |
| 5,916,192 A | 6/1999 | Nita et al. |
| 5,925,016 A | 7/1999 | Chornenky et al. |
| 5,928,186 A | 7/1999 | Homsma et al. |
| 5,931,805 A | 8/1999 | Brisken |
| 5,934,284 A | 8/1999 | Plaia et al. |
| 5,935,124 A | 8/1999 | Klumb et al. |
| 5,938,595 A | 8/1999 | Glass et al. |
| 5,941,868 A | 8/1999 | Kaplan et al. |
| 5,957,851 A | 9/1999 | Hossack |
| 5,957,882 A | 9/1999 | Nita et al. |
| 5,957,941 A | 9/1999 | Ream |
| 5,971,949 A | 10/1999 | Levin et al. |
| 5,976,120 A | 11/1999 | Chow et al. |
| 5,984,882 A | 11/1999 | Rosenschein et al. |
| 5,997,497 A | 12/1999 | Nita et al. |
| 6,001,069 A | 12/1999 | Tachibana et al. |
| 6,004,069 A | 12/1999 | Sudbury |
| 6,004,269 A | 12/1999 | Crowley et al. |
| 6,024,703 A | 2/2000 | Zanelli et al. |
| 6,024,718 A | 2/2000 | Chen et al. |
| 6,027,515 A | 2/2000 | Cimino |
| 6,033,397 A | 3/2000 | Laufer et al. |
| 6,053,868 A | 4/2000 | Geistert et al. |
| 6,059,731 A | 5/2000 | Seward |
| 6,063,069 A | 5/2000 | Cragg et al. |
| 6,066,123 A | 5/2000 | Bednarski et al. |
| 6,078,830 A | 6/2000 | Levin et al. |
| 6,088,613 A | 7/2000 | Unger |
| 6,089,573 A | 7/2000 | Udagawa |
| 6,096,000 A | 8/2000 | Tachibana et al. |
| 6,110,098 A | 8/2000 | Renirie |
| 6,110,314 A | 8/2000 | Nix et al. |
| 6,113,546 A | 9/2000 | Suorsa |
| 6,113,558 A | 9/2000 | Rosenchein et al. |
| 6,113,570 A | 9/2000 | Siegel et al. |
| 6,117,101 A | 9/2000 | Diederich et al. |
| 6,120,454 A | 9/2000 | Suorsa |
| 6,135,971 A | 10/2000 | Hutchinson |
| 6,135,976 A | 10/2000 | Tachibana et al. |
| 6,149,596 A | 11/2000 | Bancroft |
| 6,149,599 A | 11/2000 | Schlesinger |
| 6,176,842 B1 | 1/2001 | Tachibana et al. |
| 6,196,973 B1 | 3/2001 | Lazenby |
| 6,206,831 B1 | 3/2001 | Suorsa et al. |
| 6,210,356 B1 | 4/2001 | Anderson et al. |
| 6,210,393 B1 | 4/2001 | Brisken |
| 6,221,038 B1 | 4/2001 | Brisken |
| 6,228,046 B1 | 5/2001 | Brisken |
| 6,231,516 B1 | 5/2001 | Keilman |
| 6,235,024 B1 | 5/2001 | Tu |
| 6,238,347 B1 | 5/2001 | Nix et al. |
| 6,270,460 B1 | 8/2001 | McCartan et al. |
| 6,277,077 B1 | 8/2001 | Brisken et al. |
| 6,283,920 B1 | 9/2001 | Eberle |
| 6,287,271 B1 | 9/2001 | Dubrul et al. |
| 6,296,610 B1 | 10/2001 | Schneider et al. |
| 6,296,619 B1 | 10/2001 | Brisken et al. |
| 6,299,597 B1 | 10/2001 | Buscemi et al. |
| 6,309,370 B1 | 10/2001 | Haim et al. |
| 6,312,402 B1 | 11/2001 | Hansmann |
| 6,361,500 B1 | 3/2002 | Masters |
| 6,361,554 B1 | 3/2002 | Brisken |
| 6,366,719 B1 | 4/2002 | Heath et al. |
| 6,372,498 B2 | 4/2002 | Newman et al. |
| 6,379,320 B1 | 4/2002 | Lafon et al. |
| 6,387,035 B1 | 5/2002 | Jung, Jr. et al. |
| 6,387,052 B1 | 5/2002 | Quinn |
| 6,391,042 B1 | 5/2002 | Cimino |
| 6,394,956 B1 | 5/2002 | Chandrasekaran et al. |
| 6,398,772 B1 | 6/2002 | Bond et al. |
| 6,398,792 B1 | 6/2002 | O'Connor |
| 6,416,740 B1 | 7/2002 | Unger |
| 6,423,026 B1 | 7/2002 | Gesswein et al. |
| 6,433,464 B2 | 8/2002 | Jones |
| 6,437,487 B1 | 8/2002 | Mohr, III |
| 6,454,737 B1 | 9/2002 | Nita et al. |
| 6,454,757 B1 | 9/2002 | Nita et al. |
| 6,456,863 B1 | 9/2002 | Levin |
| 6,461,314 B1 | 10/2002 | Pant et al. |
| 6,464,680 B1 | 10/2002 | Brisken et al. |
| 6,471,683 B2 | 10/2002 | Drasier et al. |
| 6,478,765 B2 | 11/2002 | Siegel et al. |
| 6,494,891 B1 | 12/2002 | Cornish et al. |
| 6,503,202 B1 | 1/2003 | Hossack et al. |
| 6,506,584 B1 | 1/2003 | Chandler et al. |
| 6,508,775 B2 | 1/2003 | McKenzie et al. |
| 6,511,478 B1 | 1/2003 | Burnside et al. |
| 6,524,251 B2 | 2/2003 | Rabiner et al. |
| 6,524,271 B2 | 2/2003 | Brisken et al. |
| 6,524,300 B2 | 2/2003 | Meglin |
| 6,537,224 B2 | 3/2003 | Mauchamp et al. |
| 6,537,306 B1 | 3/2003 | Burdette et al. |
| 6,542,767 B1 | 4/2003 | McNichols et al. |
| 6,551,337 B1 | 4/2003 | Rabiner et al. |

(56) References Cited

U.S. PATENT DOCUMENTS

| | | |
|---|---|---|
| 6,558,366 B1 | 5/2003 | Drasler et al. |
| 6,560,837 B1 | 5/2003 | Hodjat et al. |
| 6,561,998 B1 | 5/2003 | Roth |
| 6,562,021 B1 | 5/2003 | Derbin et al. |
| 6,565,552 B1 | 5/2003 | Barbut |
| 6,575,922 B1 | 6/2003 | Fearnside et al. |
| 6,575,956 B1 | 6/2003 | Brisken et al. |
| 6,579,277 B1 | 6/2003 | Rabiner et al. |
| 6,579,279 B1 | 6/2003 | Rabiner et al. |
| 6,582,392 B1 | 6/2003 | Bennett et al. |
| 6,585,763 B1 | 7/2003 | Keilman |
| 6,589,182 B1 | 7/2003 | Loftman |
| 6,589,253 B1 | 7/2003 | Cornish et al. |
| 6,599,288 B2 | 7/2003 | Maguire |
| 6,605,084 B2 | 8/2003 | Acker et al. |
| 6,607,502 B1 | 8/2003 | Maguire et al. |
| 6,623,444 B2 | 9/2003 | Babaev |
| 6,635,017 B1 | 10/2003 | Moehring et al. |
| 6,635,046 B1 | 10/2003 | Barbut |
| 6,645,150 B2 | 11/2003 | Angelsen et al. |
| 6,647,755 B2 | 11/2003 | Rabiner et al. |
| 6,652,547 B2 | 11/2003 | Rabiner et al. |
| 6,660,013 B2 | 12/2003 | Rabiner et al. |
| 6,663,613 B1 | 12/2003 | Evans et al. |
| 6,676,626 B1 | 1/2004 | Bennett et al. |
| 6,682,502 B2 | 1/2004 | Bond et al. |
| 6,689,086 B1 | 2/2004 | Nita et al. |
| 6,695,781 B2 | 2/2004 | Rabiner et al. |
| 6,695,782 B2 | 2/2004 | Ranucci et al. |
| 6,695,785 B2 | 2/2004 | Brisken et al. |
| 6,711,953 B2 | 3/2004 | Hayashi et al. |
| 6,723,063 B1 | 4/2004 | Zhang et al. |
| 6,723,064 B2 | 4/2004 | Babaev |
| 6,726,698 B2 | 4/2004 | Cimino |
| 6,730,048 B1 | 5/2004 | Hare et al. |
| 6,733,451 B2 | 5/2004 | Rabiner et al. |
| 6,740,040 B1 | 5/2004 | Mandrusov et al. |
| 6,758,857 B2 | 7/2004 | Cioanta |
| 6,767,345 B2 | 7/2004 | St. Germain et al. |
| 6,824,515 B2 | 11/2004 | Suorsa et al. |
| 6,824,575 B1 | 11/2004 | Otomo et al. |
| 6,830,577 B2 | 12/2004 | Nash et al. |
| 6,849,062 B2 | 2/2005 | Kantor |
| 6,855,123 B2 | 2/2005 | Nita |
| 6,866,670 B2 | 3/2005 | Rabiner et al. |
| 6,905,505 B2 | 6/2005 | Dodson, Jr. et al. |
| 6,921,371 B2 | 7/2005 | Wilson |
| 6,929,633 B2 | 8/2005 | Evans et al. |
| 6,942,620 B2 | 9/2005 | Nita et al. |
| 6,942,677 B2 | 9/2005 | Nita et al. |
| 6,945,937 B2 | 9/2005 | Culp et al. |
| 6,958,040 B2 | 10/2005 | Oliver |
| 6,979,293 B2 | 12/2005 | Hansmann et al. |
| 6,985,771 B2 | 1/2006 | Fischell et al. |
| 7,077,820 B1 | 7/2006 | Kadziauskas et al. |
| 7,089,063 B2 | 8/2006 | Lesh et al. |
| 7,137,963 B2 | 11/2006 | Nita et al. |
| 7,141,044 B2 | 11/2006 | Gentsler |
| 7,166,098 B1 | 1/2007 | Steward et al. |
| 7,186,246 B2 | 3/2007 | Bennett et al. |
| 7,220,233 B2 | 5/2007 | Nita et al. |
| 7,220,239 B2 | 5/2007 | Wilson et al. |
| 7,309,334 B2 | 12/2007 | von Hoffmann |
| 7,335,180 B2 | 2/2008 | Nita et al. |
| 7,341,569 B2 | 3/2008 | Soltani et al. |
| 7,384,407 B2 | 6/2008 | Rodriguez et al. |
| 7,413,556 B2 | 8/2008 | Zhang et al. |
| 7,503,895 B2 | 3/2009 | Rabiner et al. |
| 7,540,852 B2 | 6/2009 | Nita et al. |
| 7,567,016 B2 | 7/2009 | Lu et al. |
| 7,604,608 B2 | 10/2009 | Nita et al. |
| 7,621,902 B2 | 11/2009 | Nita et al. |
| 7,621,929 B2 | 11/2009 | Nita et al. |
| 7,648,478 B2 | 1/2010 | Soltani et al. |
| 7,715,908 B2 | 5/2010 | Moran et al. |
| 7,727,178 B2 | 6/2010 | Wilson |
| 7,758,509 B2 | 7/2010 | Angelsen et al. |
| 7,771,372 B2 | 8/2010 | Wilson |
| 7,774,933 B2 | 8/2010 | Wilson et al. |
| 7,789,830 B2 | 9/2010 | Fujita et al. |
| 7,818,854 B2 | 10/2010 | Wilson |
| 7,828,754 B2 | 11/2010 | Abe et al. |
| 7,828,762 B2 | 11/2010 | Wilson |
| 7,862,576 B2 | 1/2011 | Gurm |
| 7,901,359 B2 | 3/2011 | Mandrusov et al. |
| 7,914,509 B2 | 3/2011 | Bennett et al. |
| 8,012,092 B2 | 9/2011 | Powers et al. |
| 8,062,566 B2 | 11/2011 | Nita et al. |
| 8,123,789 B2 | 2/2012 | Khanna |
| 8,152,753 B2 | 4/2012 | Nita et al. |
| 8,167,831 B2 | 5/2012 | Wilson |
| 8,192,363 B2 | 6/2012 | Soltani et al. |
| 8,696,612 B2 | 4/2014 | Wilson et al. |
| 8,740,835 B2 | 6/2014 | Soltani et al. |
| 8,764,700 B2 | 7/2014 | Zhang et al. |
| 8,819,928 B2 | 9/2014 | Nix et al. |
| 9,044,568 B2 | 6/2015 | Wilcox et al. |
| 9,107,590 B2 | 8/2015 | Hansmann et al. |
| 9,192,566 B2 | 11/2015 | Soltani et al. |
| 9,415,242 B2 | 8/2016 | Wilson et al. |
| 2001/0000791 A1 | 5/2001 | Suorsa et al. |
| 2001/0007861 A1 | 7/2001 | Newman |
| 2001/0007940 A1 | 7/2001 | Tu et al. |
| 2001/0025190 A1 | 9/2001 | Weber et al. |
| 2001/0037106 A1 | 11/2001 | Shadduck |
| 2001/0039419 A1 | 11/2001 | Francischelli et al. |
| 2001/0041842 A1 | 11/2001 | Eberle |
| 2002/0000763 A1 | 1/2002 | Jones |
| 2002/0019644 A1 | 2/2002 | Hastings |
| 2002/0032394 A1 | 3/2002 | Brisken et al. |
| 2002/0045890 A1 | 4/2002 | Celliers et al. |
| 2002/0052620 A1 | 5/2002 | Barbut |
| 2002/0068869 A1 | 6/2002 | Brisken et al. |
| 2002/0077550 A1 | 6/2002 | Rabiner et al. |
| 2002/0082238 A1 | 6/2002 | Newman et al. |
| 2002/0087083 A1 | 7/2002 | Nix |
| 2002/0099292 A1 | 7/2002 | Brisken et al. |
| 2002/0123787 A1 | 9/2002 | Weiss |
| 2002/0133111 A1 | 9/2002 | Shadduck |
| 2002/0188276 A1 | 12/2002 | Evans et al. |
| 2002/0193708 A1 | 12/2002 | Thompson et al. |
| 2003/0036705 A1 | 2/2003 | Hare et al. |
| 2003/0040501 A1 | 2/2003 | Newman et al. |
| 2003/0050662 A1 | 3/2003 | Don Michael |
| 2003/0065263 A1 | 4/2003 | Hare et al. |
| 2003/0069525 A1 | 4/2003 | Brisken et al. |
| 2003/0083608 A1 | 5/2003 | Evans et al. |
| 2003/0109812 A1 | 6/2003 | Cort et al. |
| 2003/0135262 A1 | 7/2003 | Dretler et al. |
| 2003/0163147 A1 | 8/2003 | Hare et al. |
| 2003/0236539 A1 | 12/2003 | Rabiner et al. |
| 2004/0001809 A1 | 1/2004 | Brisken et al. |
| 2004/0015122 A1 | 1/2004 | Zhang et al. |
| 2004/0019318 A1 | 1/2004 | Wilson et al. |
| 2004/0024393 A1 | 2/2004 | Nita et al. |
| 2004/0039311 A1 | 2/2004 | Nita et al. |
| 2004/0049148 A1 | 3/2004 | Rodriguez et al. |
| 2004/0059313 A1 | 3/2004 | Anderson et al. |
| 2004/0068189 A1 | 4/2004 | Wilson et al. |
| 2004/0097996 A1 | 5/2004 | Hare et al. |
| 2004/0122354 A1 | 6/2004 | Semba |
| 2004/0133232 A1 | 7/2004 | Rosenbluth et al. |
| 2004/0138570 A1 | 7/2004 | Nita et al. |
| 2004/0162571 A1 | 8/2004 | Rabiner et al. |
| 2004/0171981 A1 | 9/2004 | Buffen et al. |
| 2004/0220514 A1 | 11/2004 | Cafferata |
| 2004/0236350 A1 | 11/2004 | Bolduc et al. |
| 2004/0243062 A1 | 12/2004 | Henry |
| 2004/0255957 A1 | 12/2004 | Cafferata |
| 2004/0265393 A1 | 12/2004 | Unger et al. |
| 2005/0021063 A1 | 1/2005 | Hall et al. |
| 2005/0043629 A1 | 2/2005 | Rabiner et al. |
| 2005/0043753 A1 | 2/2005 | Rabiner et al. |
| 2005/0096669 A1 | 5/2005 | Rabiner et al. |

(56) References Cited

U.S. PATENT DOCUMENTS

| | | |
|---|---|---|
| 2005/0113688 A1 | 5/2005 | Nita et al. |
| 2005/0119679 A1 | 6/2005 | Rabiner et al. |
| 2005/0124877 A1 | 6/2005 | Nita et al. |
| 2005/0137520 A1 | 6/2005 | Rule et al. |
| 2005/0187513 A1 | 8/2005 | Rabiner et al. |
| 2005/0187514 A1 | 8/2005 | Rabiner et al. |
| 2005/0192558 A1 | 9/2005 | Soltani et al. |
| 2005/0197619 A1 | 9/2005 | Rule et al. |
| 2005/0209578 A1 | 9/2005 | Evans et al. |
| 2005/0215942 A1 | 9/2005 | Abrahamson et al. |
| 2005/0215946 A1 | 9/2005 | Hansmann et al. |
| 2005/0216044 A1 | 9/2005 | Hong |
| 2005/0256410 A1 | 11/2005 | Rabiner et al. |
| 2005/0288695 A1 | 12/2005 | Jenson et al. |
| 2006/0069303 A1 | 3/2006 | Couvillon |
| 2006/0106308 A1 | 5/2006 | Hansmann et al. |
| 2006/0116610 A1 | 6/2006 | Hare et al. |
| 2006/0173387 A1 | 8/2006 | Hansmann et al. |
| 2006/0184070 A1 | 8/2006 | Hansmann et al. |
| 2007/0005121 A1 | 1/2007 | Khanna |
| 2007/0037119 A1 | 2/2007 | Pal et al. |
| 2007/0038158 A1 | 2/2007 | Nita et al. |
| 2007/0066978 A1 | 3/2007 | Schafer et al. |
| 2007/0112268 A1 | 5/2007 | Zhang et al. |
| 2007/0225619 A1 | 9/2007 | Rabiner et al. |
| 2007/0239027 A1 | 10/2007 | Nita |
| 2007/0255252 A1 | 11/2007 | Mehta |
| 2007/0265560 A1 | 11/2007 | Soltani et al. |
| 2008/0045865 A1 | 2/2008 | Kislev |
| 2008/0065014 A1 | 3/2008 | McCrystle et al. |
| 2008/0109029 A1 | 5/2008 | Gurm |
| 2008/0146918 A1 | 6/2008 | Magnin et al. |
| 2008/0154181 A1 | 6/2008 | Khanna |
| 2008/0167602 A1 | 7/2008 | Nita et al. |
| 2008/0171965 A1 | 7/2008 | Soltani et al. |
| 2008/0172067 A1 | 7/2008 | Nita et al. |
| 2008/0194954 A1 | 8/2008 | Matsunaga et al. |
| 2008/0221506 A1 | 9/2008 | Rodriguez et al. |
| 2008/0262350 A1 | 10/2008 | Unger |
| 2008/0306499 A1 | 12/2008 | Katoh et al. |
| 2008/0319355 A1 | 12/2008 | Nita |
| 2008/0319376 A1 | 12/2008 | Wilcox et al. |
| 2009/0018472 A1 | 1/2009 | Soltani et al. |
| 2009/0073455 A1 | 3/2009 | Onimura |
| 2009/0105597 A1 | 4/2009 | Abraham |
| 2009/0112150 A1 | 4/2009 | Unger et al. |
| 2009/0209900 A1 | 8/2009 | Carmeli et al. |
| 2009/0216246 A1 | 8/2009 | Nita et al. |
| 2009/0221902 A1 | 9/2009 | Myhr |
| 2010/0010393 A1 | 1/2010 | Duffy et al. |
| 2010/0022920 A1 | 1/2010 | Nita et al. |
| 2010/0022944 A1 | 1/2010 | Wilcox |
| 2010/0023036 A1 | 1/2010 | Nita et al. |
| 2010/0023037 A1 | 1/2010 | Nita et al. |
| 2010/0049209 A1 | 2/2010 | Nita et al. |
| 2010/0063413 A1 | 3/2010 | Volz |
| 2010/0063414 A1 | 3/2010 | Volz |
| 2010/0081934 A1 | 4/2010 | Hansmann et al. |
| 2010/0204582 A1 | 8/2010 | Lu |
| 2010/0210940 A1 | 8/2010 | Bradley et al. |
| 2010/0222715 A1 | 9/2010 | Nita |
| 2010/0256616 A1 | 10/2010 | Katoh et al. |
| 2010/0262215 A1 | 10/2010 | Gertner |
| 2010/0292685 A1 | 11/2010 | Katoh et al. |
| 2011/0160621 A1 | 6/2011 | Nita |
| 2011/0288449 A1 | 11/2011 | Schenkengel |
| 2011/0313328 A1 | 12/2011 | Nita |
| 2011/0319927 A1 | 12/2011 | Nita |
| 2012/0016272 A1 | 1/2012 | Nita et al. |
| 2012/0041307 A1 | 2/2012 | Patel et al. |
| 2012/0059285 A1 | 3/2012 | Soltani et al. |
| 2012/0078140 A1 | 3/2012 | Nita |
| 2012/0123273 A1 | 5/2012 | Okuno et al. |
| 2012/0172795 A1 | 7/2012 | Sandhu et al. |
| 2012/0172858 A1 | 7/2012 | Harrison et al. |
| 2012/0179073 A1 | 7/2012 | Nita |
| 2012/0197277 A1 | 8/2012 | Stinis |
| 2012/0289889 A1 | 11/2012 | Genstler et al. |
| 2012/0330141 A1 | 12/2012 | Brown et al. |
| 2014/0210631 A1 | 7/2014 | Zavis |
| 2014/0236118 A1 | 8/2014 | Unser et al. |
| 2014/0343483 A1 | 11/2014 | Zhang et al. |
| 2016/0361528 A1 | 12/2016 | Kanz et al. |

FOREIGN PATENT DOCUMENTS

| | | |
|---|---|---|
| EP | 0 629 382 | 12/1994 |
| EP | 0 744 189 | 11/1996 |
| EP | 0 746 245 | 12/1996 |
| EP | 1 090 658 | 4/2001 |
| EP | 1 453 425 | 9/2004 |
| EP | 1 647 232 | 4/2006 |
| JP | 52-115591 | 9/1977 |
| JP | 02-180275 | 7/1990 |
| WO | WO 92/000113 | 1/1992 |
| WO | WO 95/001751 | 1/1995 |
| WO | WO 95/005866 | 3/1995 |
| WO | WO 95/026777 | 10/1995 |
| WO | WO 96/004955 | 2/1996 |
| WO | WO 96/027341 | 9/1996 |
| WO | WO 96/029935 | 10/1996 |
| WO | WO 96/036286 | 11/1996 |
| WO | WO 97/019645 | 6/1997 |
| WO | WO 98/011826 | 3/1998 |
| WO | WO 89/004142 | 5/1998 |
| WO | WO 98/018391 | 5/1998 |
| WO | WO 98/048711 | 11/1998 |
| WO | WO 98/056462 | 12/1998 |
| WO | WO 99/032184 | 7/1999 |
| WO | WO 99/033500 | 7/1999 |
| WO | WO 99/034858 | 7/1999 |
| WO | WO 99/039647 | 8/1999 |
| WO | WO 99/044512 | 9/1999 |
| WO | WO 00/000095 | 1/2000 |
| WO | WO 00/038580 | 7/2000 |
| WO | WO 00/069341 | 11/2000 |
| WO | WO 01/054754 | 8/2001 |
| WO | WO 01/087174 | 11/2001 |
| WO | WO 01/095788 | 12/2001 |
| WO | WO 02/013678 | 2/2002 |
| WO | WO 02/015803 | 2/2002 |
| WO | WO 02/015804 | 2/2002 |
| WO | WO 03/051208 | 6/2003 |
| WO | WO 2005/027756 | 3/2005 |
| WO | WO 2005/084552 | 9/2005 |
| WO | WO 2005/084553 | 9/2005 |
| WO | WO 2008/052186 | 5/2008 |
| WO | WO 2015/074036 | 5/2015 |

OTHER PUBLICATIONS

Hynynen et al.; "Small Cylindrical Ultrasound Sources for Induction of Hyperthermia Via Body Cavities or Interstitial Implants", Arizona Cancer Center and Department of Radiation Oncology, University of Arizona Health Sciences Center; vol. 9, No. 2, 1993 pp. 263-274.

International Search Report and Written Opinion in Application No. PCT/US02/038527, dated Jul. 25, 2003.

Lee et al.; "Arrays of Multielement Ultrasound Applicators for Interstitial Hyperthermia"; IEEE Transactios on biomedical Engineering; vol. 46, No. 7, Jul. 1999, pp. 880-890.

Lin et al., "Comparison of Percutaneous Ultrasound-Accelerated Thrombolysis versus Catheter-Directed Thrombolysis in Patients with Acute Massive Pulmonary Embolism," Vascular, 2009, vol. 17, No. 3, pp. S137-S147.

Official Communication in European Application No. 05027733.4, dated Sep. 23, 2009.

Schäfer et al., "Influence of Ultrasound Operating Parameters on Ultrasound-Induced Thrombolysis In Vitro," Ultrasound in Medicine and Biology, vol. 31, No. 6, Mar. 2005, pp, 841-847.

(56) References Cited

OTHER PUBLICATIONS

Tsetis et al., "Potential Benefits From Heating the High-Dose Rtpa Boluses Used in Catheter-Directed Thrombolysis for Acute/Subacute Lower Limb Ischemia", Journal of Endovascular Therapy, 2003, vol. 10, pp. 739-744.

* cited by examiner

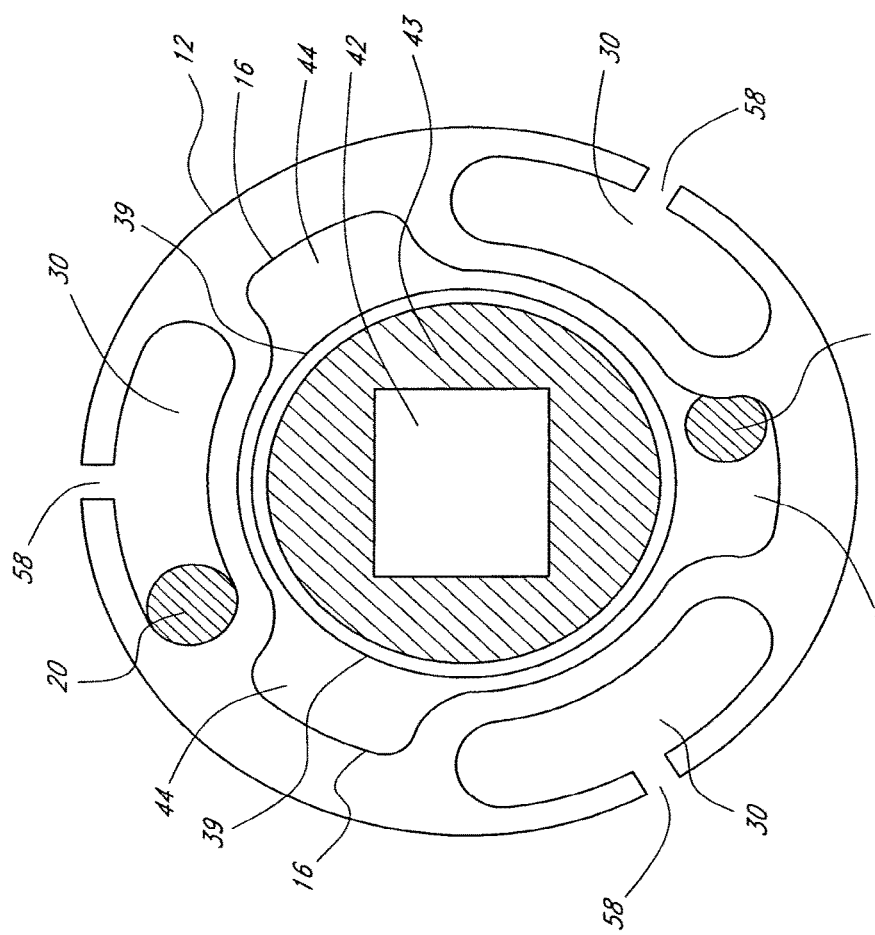

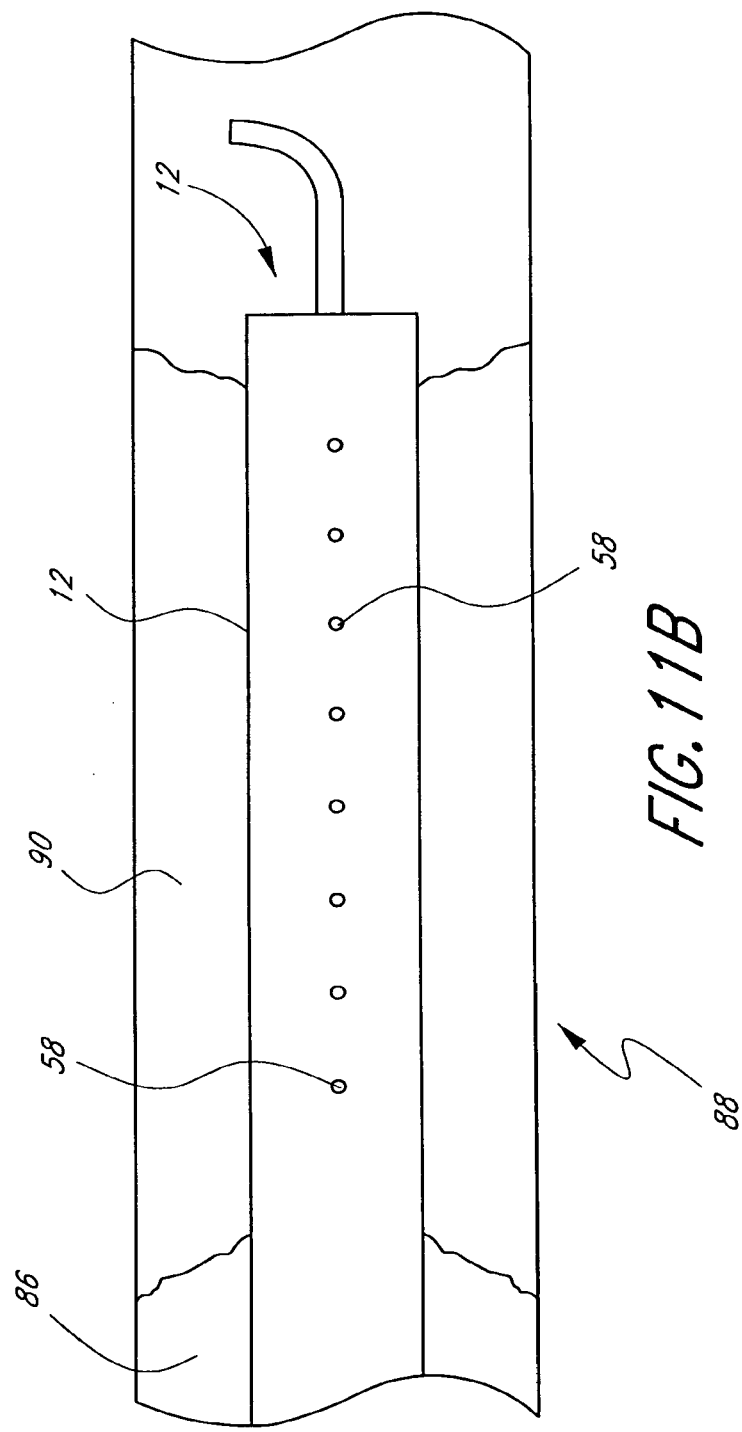

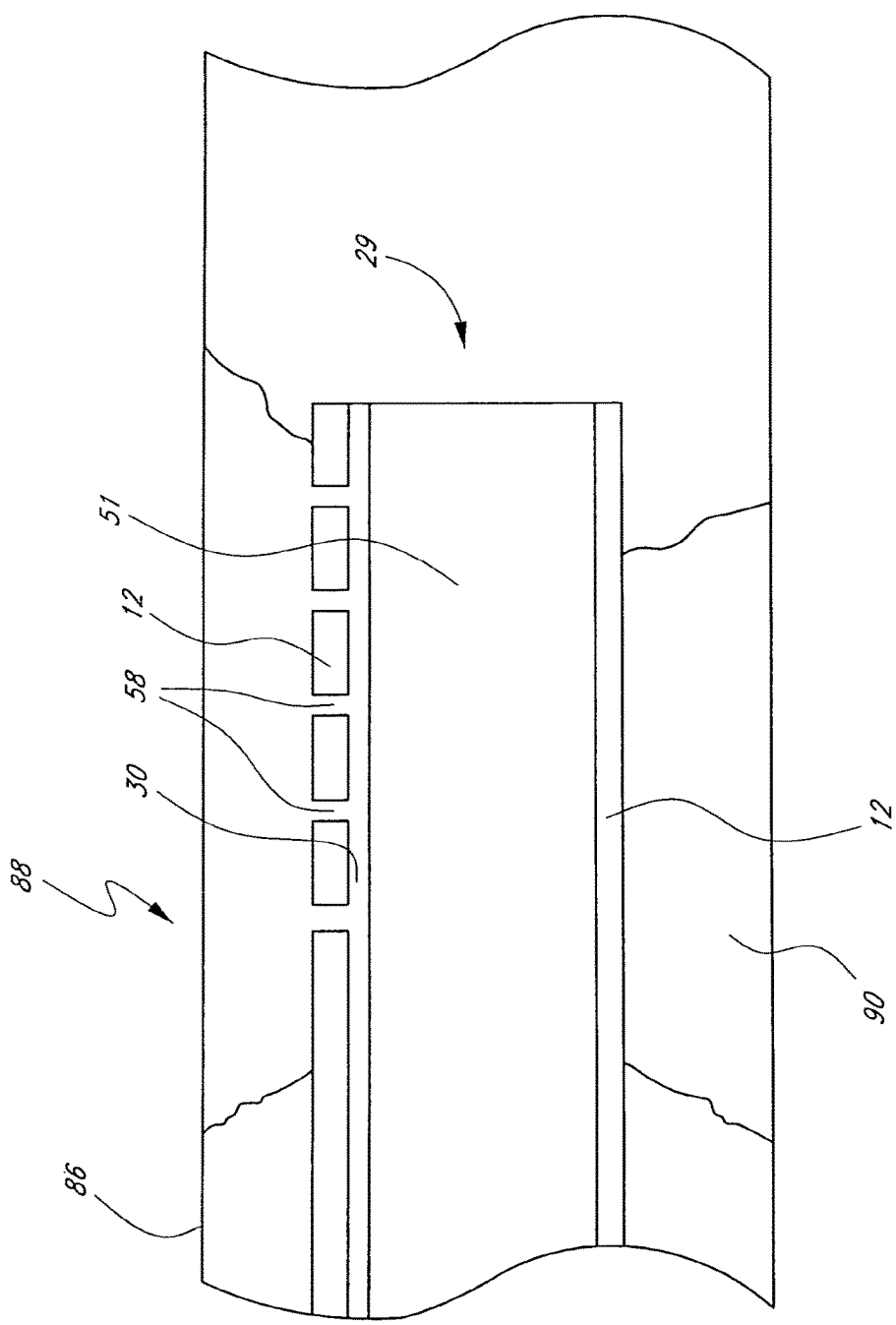

US 10,080,878 B2

CATHETER WITH MULTIPLE ULTRASOUND RADIATING MEMBERS

PRIORITY APPLICATIONS

This application is a continuation of U.S. patent application Ser. No. 14/196,225, filed Mar. 4, 2014, now U.S. Pat. No. 9,415,242, which is a continuation of U.S. patent application Ser. No. 13/431,798, filed Mar. 27, 2012, now U.S. Pat. No. 8,696,612, which is a continuation of U.S. patent application Ser. No. 12/762,254, filed Apr. 16, 2010, now U.S. Pat. No. 8,167,832, which is a divisional of U.S. patent application Ser. No. 11/643,471, filed Dec. 21, 2006, now U.S. Pat. No. 7,727,178, which is a divisional of U.S. patent application Ser. No. 10/309,388, filed Dec. 3, 2002, now U.S. Pat. No. 7,220,239, which claims the benefit of U.S. Provisional Patent Application No. 60/336,744, filed Dec. 3, 2001, U.S. Provisional Patent Application No. 60/336,630, filed Dec. 3, 2001, and U.S. Provisional Patent Application No. 60/394,093, filed Jul. 3, 2002. The entire disclosure of all of these priority documents is hereby incorporated by reference in its entirety.

STATEMENT REGARDING FEDERALLY SPONSORED R&D

The invention was made with government support under Grant No. NIH R44 HL057739 awarded by the National Institutes of Health. The government has certain rights in the invention.

BACKGROUND OF THE INVENTION

Field of the Invention

The present invention relates generally to an ultrasonic catheter and more specifically to an ultrasonic catheter configured to deliver ultrasonic energy and a therapeutic compound to a treatment site.

Description of the Related Art

Several medical applications use ultrasonic energy. For example, U.S. Pat. Nos. 4,821,740, 4,953,565 and 5,007,438 disclose the use of ultrasonic energy to enhance the effect of various therapeutic compounds. An ultrasonic catheter can be used to deliver ultrasonic energy and a therapeutic compound to a treatment site in a patient's body. Such an ultrasonic catheter typically includes an ultrasound assembly configured to generate ultrasonic energy and a fluid delivery lumen for delivering the therapeutic compound to the treatment site.

As taught in U.S. Pat. No. 6,001,069, such ultrasonic catheters can be used to treat human blood vessels that have become partially or completely occluded by plaque, thrombi, emboli or other substances that reduce the blood carrying capacity of the vessel. To remove or reduce the occlusion, the ultrasonic catheter is used to deliver solutions containing dissolution compounds directly to the occlusion site. Ultrasonic energy generated by the ultrasound assembly enhances the therapeutic effect of the dissolution compounds. For example, in one application of such an ultrasonic catheter, an ultrasound-enhanced thrombolytic therapy dissolves blood clots in arteries and veins in the treatment of diseases such as peripheral arterial occlusion or deep vein thrombosis. In such applications, ultrasonic energy enhances thrombolysis with agents such as urokinase, tissue plasminogen activator ("TPA") and the like.

Ultrasonic catheters can also be used to enhance gene therapy at a treatment site within the patient's body. For example, U.S. Pat. No. 6,135,976 discloses an ultrasonic catheter having one or more expandable sections capable of occluding a section of a body lumen, such as a blood vessel. A gene therapy composition is then delivered to the occluded vessel through the catheter fluid delivery lumen. Ultrasonic energy generated by the ultrasound assembly is applied to the occluded vessel, thereby enhancing the delivery of a genetic composition into the cells of the occluded vessel.

Ultrasonic catheters can also be used to enhance delivery and activation of light activated drugs. For example, U.S. Pat. No. 6,176,842 discloses methods for using an ultrasonic catheter to treat biological tissues by delivering a light activated drug to the biological tissues and exposing the light activated drug to ultrasound energy.

SUMMARY OF THE INVENTION

In certain medical procedures, it is desirable to provide ultrasonic energy along a substantial length of a body lumen. For example, long segment peripheral arterial occlusions, such as those in the arteries of the leg, may have an axial length in the range of 10 to 50 cm. To date, it has been difficult to design an ultrasonic catheter capable of efficiently applying ultrasound energy over such lengths.

One method for emitting ultrasonic energy over such lengths is to provide the ultrasonic catheter with a plurality of ultrasonic transducers spaced along a distal region of the catheter. Such an arrangement faces several technical hurdles. For example, because the ultrasonic transducers are relatively rigid, the catheter may become too inflexible to be navigated through the lumens of the patient's body. One solution is to use smaller transducers. However, smaller transducers may not be capable of producing sufficient energy at the proper frequency to enhance the therapeutic affect of a therapeutic agent.

Another solution is disclosed in U.S. Pat. No. 6,296,610. This patent discloses a catheter with a plurality of transducers that are moved back and forth within the catheter through the treatment zone. However, this arrangement is generally undesirable because it requires a translation system for moving the ultrasonic elements within the catheter.

Additionally, for ease of manufacturing and reduced costs, it is generally desirable to use ultrasonic transducers that are in the form of rectangular bars as compared to, for example, cylindrical transducers. However, such arrangements should still generate a therapeutically effective ultrasonic energy field.

A need, therefore, exists for an improved ultrasonic catheter capable of providing ultrasonic energy over a substantial length of a body lumen with little or no movement of the ultrasonic elements within the patient during treatment. Such a catheter preferably uses flat rectangular ultrasonic transducers.

As such, according to one embodiment of the present invention, a catheter system for delivering ultrasonic energy and a therapeutic compound to a treatment site within a body lumen comprises a tubular body. The tubular body has a proximal end, a distal end and an energy delivery section positioned between the proximal end and the distal end. The catheter system further comprises a fluid delivery lumen extending at least partially through the tubular body. The fluid delivery lumen has at least one outlet in the energy delivery section. The catheter system further comprises an inner core configured for insertion into the tubular body. The inner core comprises an elongate electrical conductor having a plurality of flattened regions. Each flattened region has a first flat side and a second flat side opposite the first flat side. The inner core further comprises a plurality of ultrasound radiating members mounted in pairs to the flattened regions of the elongate electrical conductor. A first ultrasound radiating member is mounted to the first flat side of the elongate electrical conductor, and a second ultrasound radiating member is mounted to the second flat side of the elongate electrical conductor. The inner core further comprises wiring such that a voltage can be applied from the elongate electrical conductor across the first and second ultrasound radiating members. The first and second ultrasound radiating members can be driven simultaneously.

According to another embodiment of the present invention, a catheter system for delivering ultrasonic energy to a treatment site comprises a tubular body. The tubular body has a proximal end, a distal end and a treatment zone located between the distal end and the proximal end. The catheter system further comprises an ultrasonic assembly positioned within the treatment zone. The ultrasonic assembly comprises an electrical conductor and an ultrasonic transducer pair. The ultrasonic transducer pair includes a first ultrasound transducer having a first portion and a second ultrasound transducer having a second portion. The first portion of the first transducer and the second portion of the second transducer face each other and are electrically coupled to the electrical conductor.

According to another embodiment of the present invention, a catheter system for delivering ultrasonic energy to a treatment site comprises a tubular body. The tubular body has a proximal end, a distal end and a treatment zone located between the distal and proximal ends. The catheter system further comprises an ultrasonic assembly positioned within the treatment zone. The ultrasonic assembly comprises an electrical conductor and an ultrasonic transducer pair. The ultrasonic transducer pair includes a rectangular solid first ultrasonic element and a rectangular solid second ultrasonic element. The first and second ultrasonic elements are mounted on opposite sides of the electrical conductor.

According to another embodiment of the present invention, an apparatus comprises an elongate tubular body having a fluid delivery lumen. The apparatus further comprises an inner core configured for insertion into the tubular body. The inner core comprises a common wire and a plurality of ultrasound radiating members. The plurality of ultrasound radiating members are positioned and electrically coupled to the common wire in pairs. The apparatus further comprises a control system configured to drive each pair of ultrasound radiating members.

According to another embodiment of the present invention, a method of delivering ultrasonic energy and a therapeutic compound to a treatment site comprises providing a catheter with a plurality of ultrasound radiating members. The plurality of ultrasound radiating members are allocated into electrical groups comprising more than one ultrasound radiating member. The method further comprises independently driving each group of ultrasonic radiating members. The method further comprises delivering the therapeutic compound through the catheter to the treatment site.

According to another embodiment of the present invention, an ultrasonic catheter comprises a tubular body. The tubular body has a proximal end, a distal end and a treatment zone located between the distal end and the proximal end. The ultrasonic catheter further comprises a plurality of fluid delivery lumens defined within the tubular body. The ultrasonic catheter further comprises an inner core comprising at least one ultrasound radiating element. The ultrasonic catheter further comprises a plurality of cooling fluid channels defined between at least an inner surface of the tubular body and an outer surface of the inner core. Each cooling fluid channel is positioned generally radially between two fluid delivery lumens.

According to another embodiment of the present invention, an ultrasonic catheter system comprises a tubular body. The tubular body has a proximal end, a distal end and a treatment zone located between the distal end and the proximal end. The ultrasonic catheter system further comprises a fluid delivery lumen. The ultrasonic catheter system further comprises at least one ultrasound radiating element positioned in the treatment zone. The ultrasonic catheter system further comprises wiring electrically coupled to the at least one ultrasound radiating element. The wiring extends through the tubular body and terminates at a connector. The ultrasonic catheter system further comprises a control system. The control system comprises external circuitry and an isolation pod. The isolation pod is configured to be electrically connected to the connector. The isolation pod is also positioned between the tubular body and the external system. The isolation pod comprises an isolation barrier and circuitry for driving the ultrasound radiating element.

According to another embodiment of the present invention, an ultrasonic catheter comprises a tubular body. The tubular body has a proximal end, a distal end and a treatment zone located between the distal end and the proximal end. The ultrasonic catheter further comprises at least one fluid delivery lumen incorporated into the tubular body. The ultrasonic catheter further comprises a plurality of ultrasound radiating members mounted within an inner core. The inner core is positioned within the tubular body such that at least one of the ultrasound radiating members is located within the treatment zone. The ultrasonic catheter further comprises means for independently driving each of the ultrasound transducers.

For purposes of summarizing the invention and the advantages achieved over the prior art, certain objects and advantages of the invention have been described above. It is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

All of these embodiments are intended to be within the scope of the invention herein disclosed. These and other embodiments of the present invention will become readily apparent to those skilled in the art from the following detailed description of the preferred embodiments having reference to the attached figures, the invention not being limited to any particular preferred embodiment(s) disclosed.

BRIEF DESCRIPTION OF THE DRAWINGS

FIG. 8 illustrates the energy delivery section of the inner core of FIG. 4 positioned within the energy delivery section of the tubular body of FIG. 2.

FIG. 11B is a side view of the distal end of an ultrasonic catheter positioned at the treatment site of FIG. 11A.

FIG. 11C is a cross-sectional view of the distal end of the ultrasonic catheter of FIG. 11B positioned at the treatment site before a treatment.

DETAILED DESCRIPTION OF PREFERRED EMBODIMENTS

Figure 1:
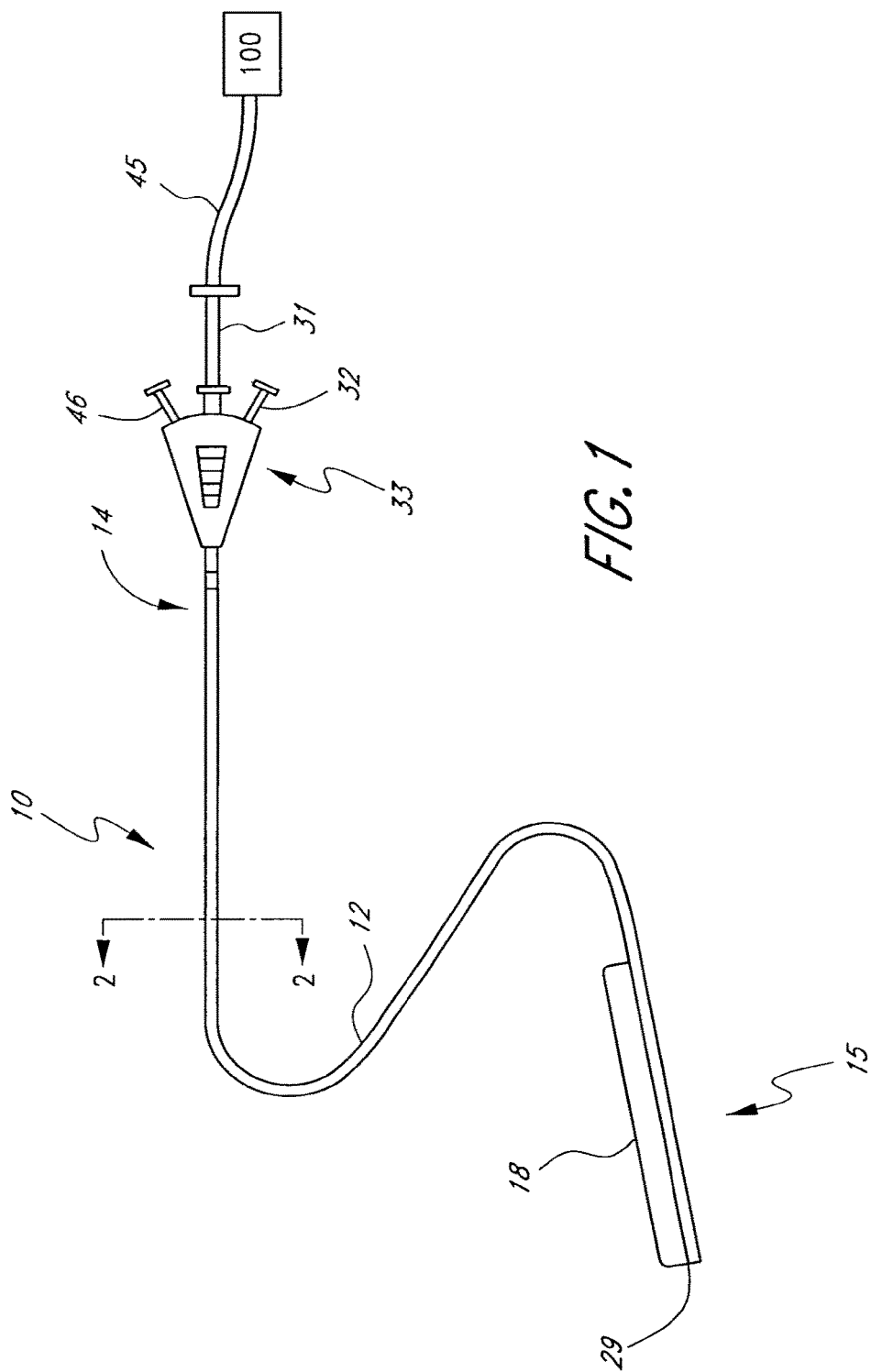
FIG. 1 is a schematic illustration of an ultrasonic catheter configured for insertion into large vessels of the human body.

As described above, it is desired to provide an ultrasonic catheter having various features and advantages. Examples of such features and advantages include the ability to apply ultrasonic energy to a treatment site. In another embodiments, the catheter has the ability to deliver a therapeutic compound to the treatment site. Preferred embodiments of an ultrasonic catheter having certain of these features and advantages are described herein. Methods of using such an ultrasonic catheter are also described herein.

The ultrasonic catheters described herein can be used to enhance the therapeutic effects of therapeutic compounds at a treatment site within a patient's body. As used herein, the term "therapeutic compound" refers broadly, without limitation, to a drug, medicament, dissolution compound, genetic material or any other substance capable of effecting physiological functions. Additionally, any mixture comprising any such substances is encompassed within this definition of "therapeutic compound", as well as any substance falling within the ordinary meaning of these terms. The enhancement of the effects of therapeutic compounds using ultrasonic energy is described in U.S. Pat. Nos. 5,318,014, 5,362,309, 5,474,531, 5,628,728, 6,001,069 and 6,210,356, the entire disclosure of which are hereby incorporated by herein by reference. Specifically, for applications that treat human blood vessels that have become partially or completely occluded by plaque, thrombi, emboli or other substances that reduce the blood carrying capacity of a vessel, suitable therapeutic compounds include, but are not limited to, an aqueous solution containing Heparin, Uronkinase, Streptokinase, TPA and BB-10153 (manufactured by British Biotech, Oxford, UK).

Certain features and aspects of the ultrasonic catheters disclosed herein may also find utility in applications where the ultrasonic energy itself provides a therapeutic effect. Examples of such therapeutic effects include preventing or reducing stenosis and/or restenosis; tissue ablation, abrasion or disruption; promoting temporary or permanent physiological changes in intracellular or intercellular structures; and rupturing micro-balloons or micro-bubbles for therapeutic compound delivery. Further information about such methods can be found in U.S. Pat. Nos. 5,261,291 and 5,431,663, the entire disclosure of which are hereby incorporated by herein by reference.

The ultrasonic catheters described herein are configured for applying ultrasonic energy over a substantial length of a body lumen, such as, for example, the larger vessels located in the leg. However, it should be appreciated that certain features and aspects of the present invention may be applied to catheters configured to be inserted into the small cerebral vessels, in solid tissues, in duct systems and in body cavities. Additional embodiments that may be combined with certain features and aspects of the embodiments described herein are described in U.S. patent application, Attorney Docket EKOS.026A, entitled "Ultrasound Assembly For Use With A Catheter" and filed Nov. 7, 2002, the entire disclosure of which is hereby incorporated herein by reference.

With initial reference to FIG. 1 schematically illustrates an ultrasonic catheter 10 configured for use in the large vessels of a patient's anatomy. For example, the ultrasonic catheter 10 illustrated in FIG. 1 can be used to treat long segment peripheral arterial occlusions, such as those in the vascular system of the leg.

As illustrated in FIG. 1, the ultrasonic catheter 10 generally comprises a multi-component, elongate flexible tubular body 12 having a proximal region 14 and a distal region 15. The tubular body 12 includes a flexible energy delivery section 18 located in the distal region 15 of the catheter 10. The tubular body 12 and other components of the catheter 10 can be manufactured in accordance with any of a variety of techniques well known in the catheter manufacturing field. Suitable materials and dimensions can be readily selected based on the natural and anatomical dimensions of the treatment site and on the desired percutaneous access site.

For example, in a preferred embodiment the proximal region 14 of the tubular body 12 comprises a material that has sufficient flexibility, kink resistance, rigidity and structural support to push the energy delivery section 18 through the patient's vasculature to a treatment site. Examples of such materials include, but are not limited to, extruded polytetrafluoroethylene ("PTFE"), polyethylenes ("PE"), polyamides and other similar materials. In certain embodiments, the proximal region 14 of the tubular body 12 is reinforced by braiding, mesh or other constructions to provide increased kink resistance and pushability. For example, nickel titanium or stainless steel wires can be placed along or incorporated into the tubular body 12 to reduce kinking.

In an embodiment configured for treating thrombus in the arteries of the leg, the tubular body 12 has an outside diameter between about 0.060 inches and about 0.075 inches. In another embodiment, the tubular body 12 has an outside diameter of about 0.071 inches. In certain embodiments, the tubular body 12 has an axial length of approximately 105 centimeters, although other lengths may by appropriate for other applications.

The energy delivery section 18 of the tubular body 12 preferably comprises a material that is thinner than the material comprising the proximal region 14 of the tubular body 12 or a material that has a greater acoustic transparency. Thinner materials generally have greater acoustic transparency than thicker materials. Suitable materials for the energy delivery section 18 include, but are not limited to, high or low density polyethylenes, urethanes, nylons, and the like. In certain modified embodiments, the energy delivery section 18 may be formed from the same material or a material of the same thickness as the proximal region 18.

In certain embodiments, the tubular body 12 is divided into at least three sections of varying stiffness. The first section, which preferably includes the proximal region 14, has a relatively higher stiffness. The second section, which is located in an intermediate region between the proximal region 14 and the distal region 15 of the tubular body 12, has a relatively lower stiffness. This configuration further facilitates movement and placement of the catheter 10. The third section, which preferably includes the energy delivery section 18, is generally lower stiffness than the second section in spite of the presence of the ultrasound radiating members 40.

Figure 2:
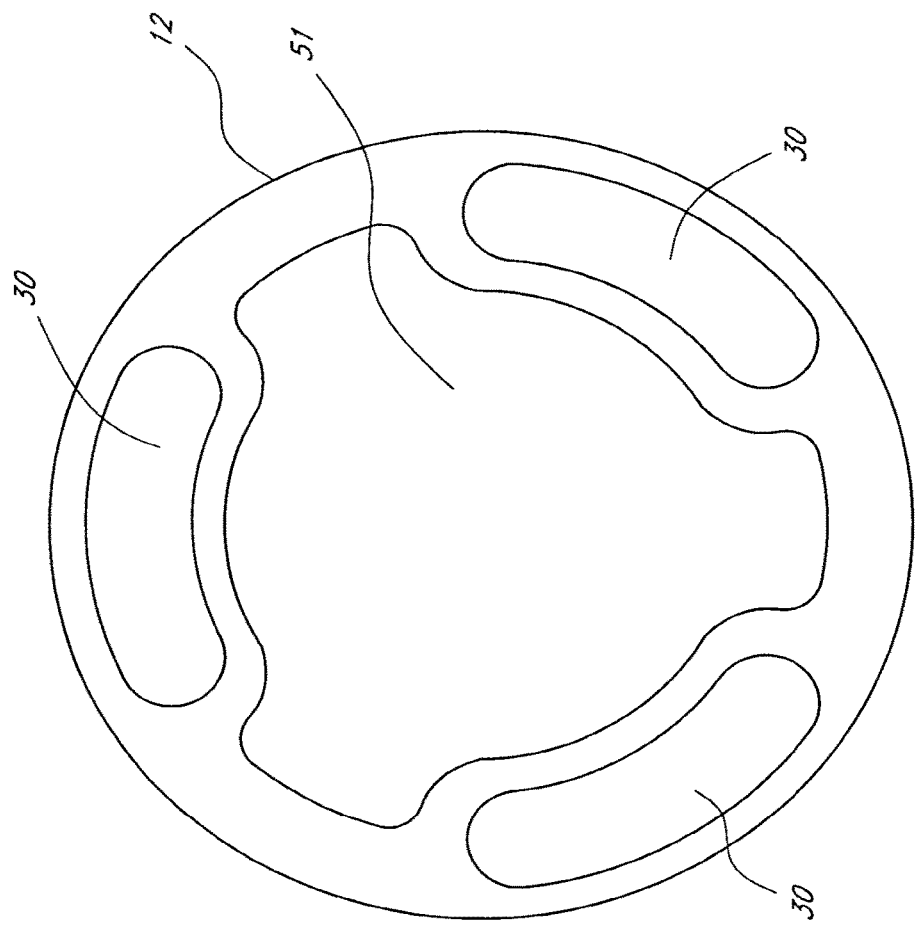
FIG. 2 is a cross-sectional view of the ultrasonic catheter of FIG. 1 taken along line 2-2.

FIG. 2 illustrates a cross section of the tubular body 12 taken along line 2-2 in FIG. 1. In the embodiment illustrated in FIG. 2, three fluid delivery lumens 30 are incorporated into the tubular body 12. In other embodiments, more or fewer fluid delivery lumens can be incorporated into the tubular body 12. The arrangement of the fluid delivery lumens 30 preferably provides a hollow central lumen 51 passing through the tubular body 12. The cross-section of the tubular body 12, as illustrated in FIG. 2, is preferably substantially constant along the length of the catheter 10. Thus, in such embodiments, substantially the same cross-section is present in both the proximal region 14 and the distal region 15 of the catheter 10, including the energy delivery section 18.

In certain embodiments, the central lumen 51 has a minimum diameter greater than about 0.030 inches. In another embodiment, the central lumen 51 has a minimum diameter greater than about 0.037 inches. In one preferred embodiment, the fluid delivery lumens 30 have dimensions of about 0.026 inches wide by about 0.0075 inches high, although other dimensions may be used in other applications.

As described above, the central lumen 51 preferably extends through the length of the tubular body 12. As illustrated in FIG. 1, the central lumen 51 preferably has a distal exit port 29 and a proximal access port 31. The proximal access port 31 forms part of the backend hub 33, which is attached to the proximal region 14 of the catheter 10. The backend hub preferably further comprises cooling fluid fitting 46, which is hydraulically connected to the central lumen 51. The backend hub 33 also preferably comprises a therapeutic compound inlet port 32, which is in hydraulic connection with the fluid delivery lumens 30, and which can be hydraulically coupled to a source of therapeutic compound via a hub such as a Luer fitting.

Figure 3:
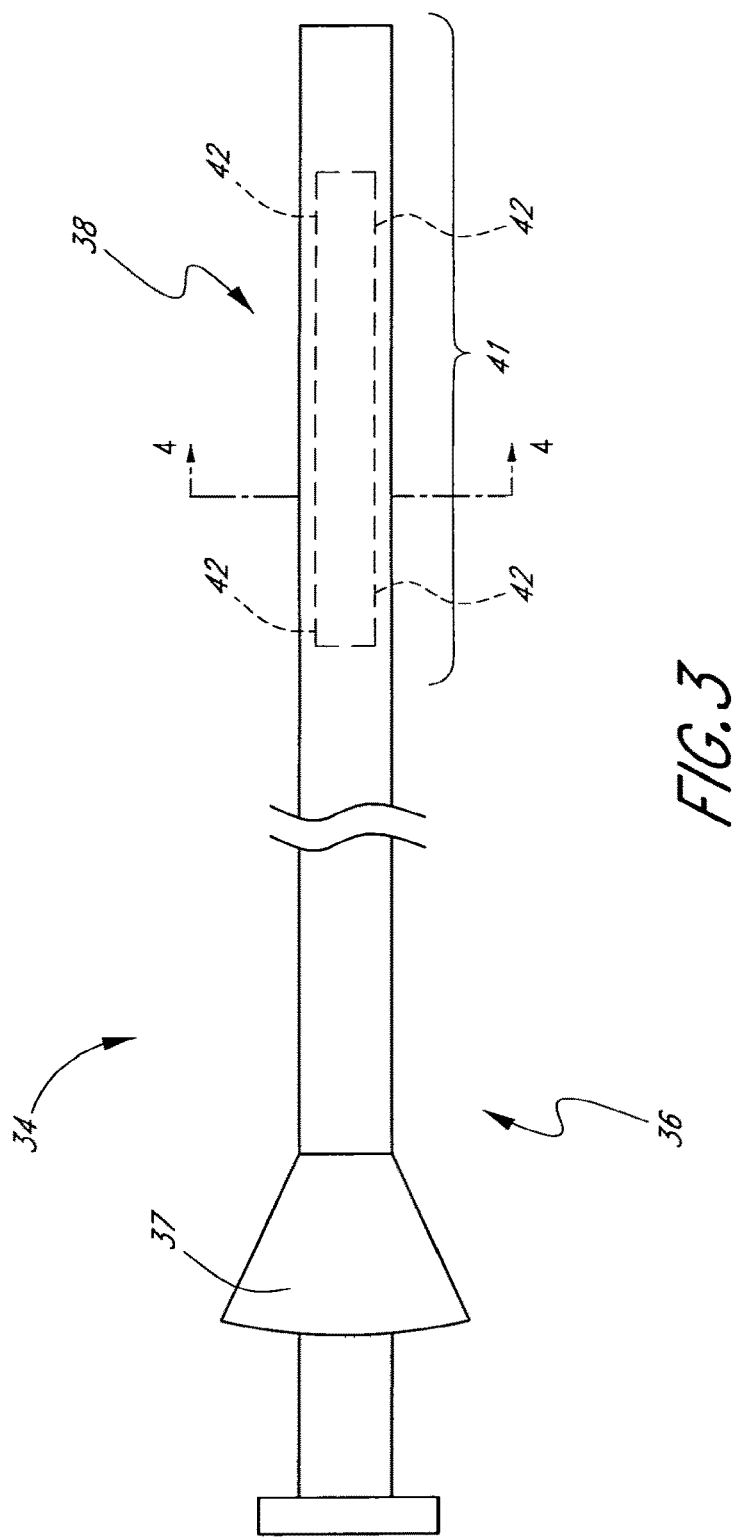
FIG. 3 is a schematic illustration of an elongate inner core configured to be positioned within the central lumen of the catheter illustrated in FIG. 2.

The central lumen 51 is configured to receive an elongate inner core 34 of which a preferred embodiment is illustrated in FIG. 3. The elongate inner core 34 preferably comprises a proximal region 36 and a distal region 38. Proximal hub 37 is fitted on the inner core 34 at one end of the proximal region 36. One or more ultrasound radiating members are positioned within an inner core energy delivery section 41 located within the distal region 38. The ultrasound radiating members 40 form an ultrasound assembly 42, which will be described in detail below.

Figure 4:
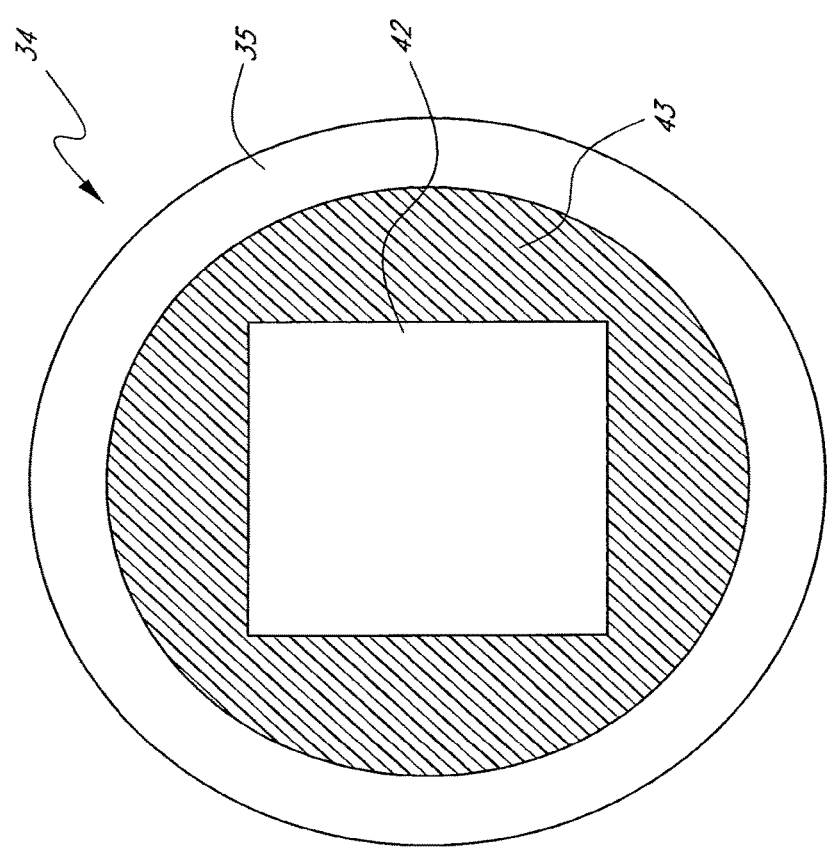
FIG. 4 is a cross-sectional view of the elongate inner core of FIG. 3 taken along line 4-4.

As shown in the cross-section illustrated in FIG. 4, which is taken along lines 4-4 in FIG. 3, the inner core 34 preferably has a cylindrical shape, with an outer diameter that permits the inner core 34 to be inserted into the central lumen 51 of the tubular body 12 via the proximal access port 31. Suitable outer diameters of the inner core 34 include, but are not limited to, about 0.010 inches to about 0.100 inches. In another embodiment, the outer diameter of the inner core 34 is between about 0.020 inches and about 0.080 inches. In yet another embodiment, the inner core 34 has an outer diameter of about 0.035 inches.

Still referring to FIG. 4, the inner core 34 preferably comprises a cylindrical outer body 35 that houses the ultrasound assembly 42. The ultrasound assembly 42 comprises wiring and ultrasound radiating members, described in greater detail in FIGS. 5 through 7D, such that the ultrasound assembly 42 is capable of radiating ultrasonic energy from the energy delivery section 41 of the inner core 34. The ultrasound assembly 42 is electrically connected to the backend hub 33, where the inner core 34 can be connected to a control system 100 via cable 45 (illustrated in FIG. 1). Preferably, an electrically insulating potting material 43 fills the inner core 34, surrounding the ultrasound assembly 42, thus preventing movement of the ultrasound assembly 42 with respect to the outer body 35. In one embodiment, the thickness of the outer body 35 is between about 0.0002 inches and 0.010 inches. In another embodiment, the thickness of the outer body 35 is between about 0.0002 inches and 0.005 inches. In yet another embodiment, the thickness of the outer body 35 is about 0.0005 inches.

Figure 5:
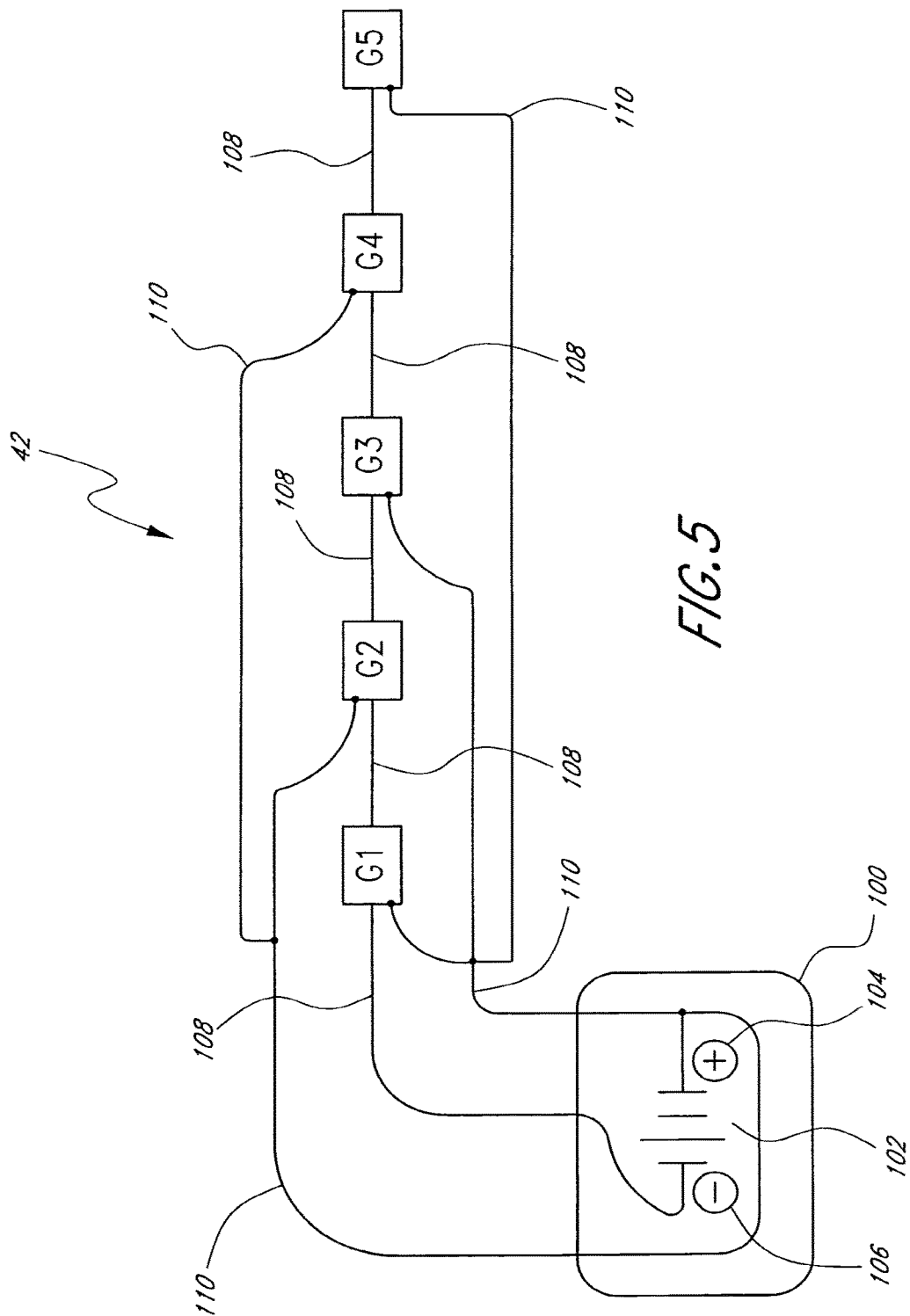
FIG. 5 is a schematic wiring diagram illustrating a preferred technique for electrically connecting five groups of ultrasound radiating members to form an ultrasound assembly.
Figure 6:
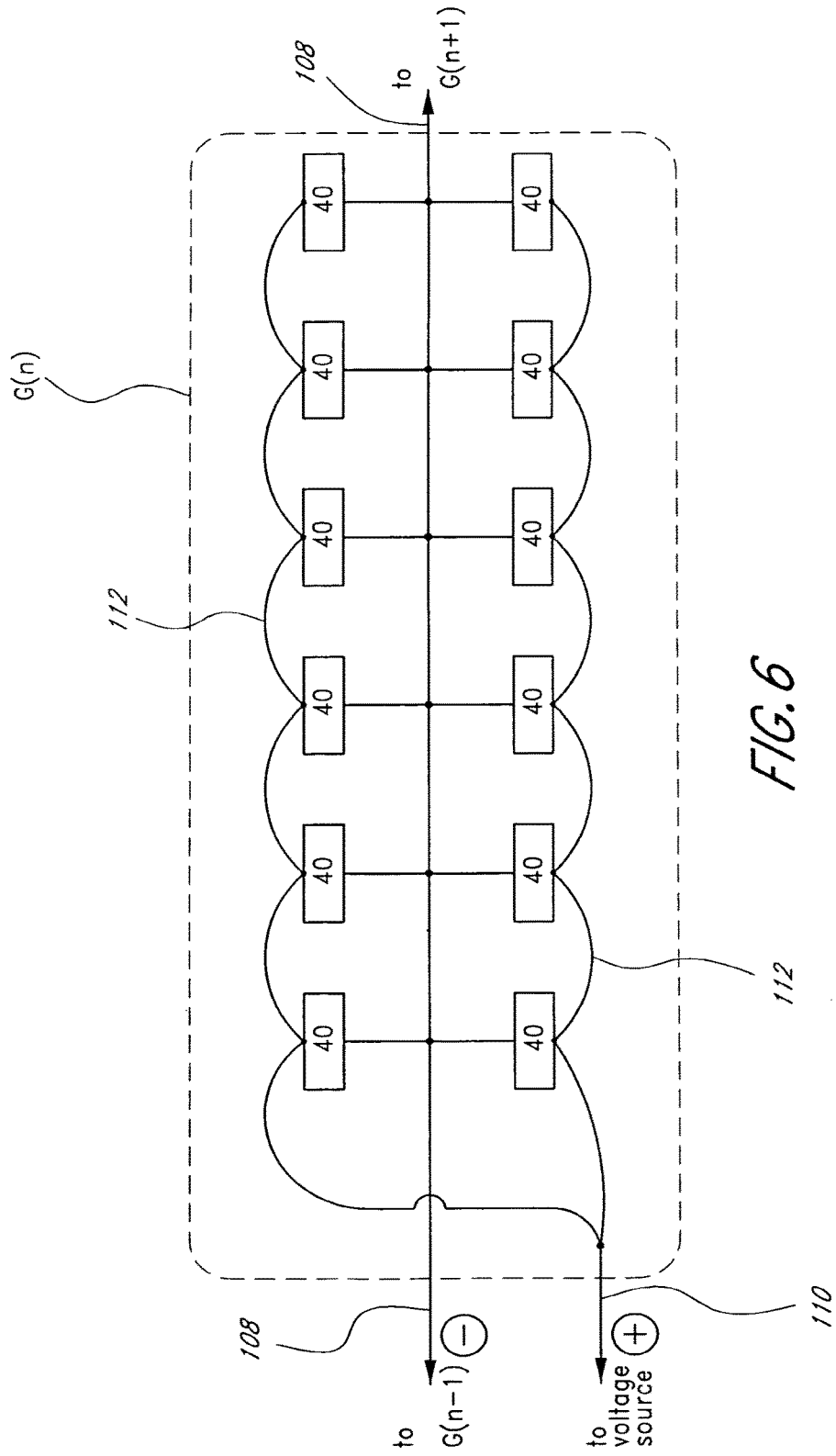
FIG. 6 is a schematic wiring diagram illustrating a preferred technique for electrically connecting one of the groups of FIG. 5.

In a preferred embodiment, the ultrasound assembly 42 comprises a plurality of ultrasound radiating members 40 that are divided into one or more groups. For example, FIGS. 5 and 6 are schematic wiring diagrams illustrating one technique for connecting five groups of ultrasound radiating members 40 to form the ultrasound assembly 42. As illustrated in FIG. 5, the ultrasound assembly 42 comprises five groups G1, G2, G3, G4, G5 of ultrasound radiating members 40 that are electrically connected to each other. The five groups are also electrically connected to the control system 100.

As used herein, the terms "ultrasonic energy", "ultrasound" and "ultrasonic" are broad terms, having their ordinary meanings, and further refer to, without limitation, mechanical energy transferred through longitudinal pressure or compression waves. Ultrasonic energy can be emitted as continuous or pulsed waves, depending on the requirements of a particular application. Additionally, ultrasonic energy can be emitted in waveforms having various shapes, such as sinusoidal waves, triangle waves, square waves, or other wave forms. Ultrasonic energy includes sound waves. In certain embodiments, the ultrasonic energy has a frequency between about 20 kHz and about 20 MHz. For example, in one embodiment, the waves have a frequency between about 500 kHz and about 20 MHz. In another embodiment, the waves have a frequency between about 1 MHz and about 3 MHz. In yet another embodiment, the waves have a frequency of about 2 MHz. The average acoustic power is between about 0.01 watts and 300 watts. In one embodiment, the average acoustic power is about 15 watts.

As used herein, the term "ultrasound radiating member" refers to any apparatus capable of producing ultrasonic energy. For example, in one embodiment, an ultrasound radiating member comprises an ultrasonic transducer, which converts electrical energy into ultrasonic energy. A suitable example of an ultrasonic transducer for generating ultrasonic energy from electrical energy includes, but is not limited to, piezoelectric ceramic oscillators. Piezoelectric ceramics typically comprise a crystalline material, such as quartz, that change shape when an electrical current is applied to the material. This change in shape, made oscillatory by an oscillating driving signal, creates ultrasonic sound waves. In other embodiments, ultrasonic energy can be generated by an ultrasonic transducer that is remote from the ultrasound radiating member, and the ultrasonic energy can be transmitted, via, for example, a wire that is coupled to the ultrasound radiating member.

Still referring to FIG. 5, the control circuitry 100 preferably comprises, among other things, a voltage source 102. The voltage source 102 comprises a positive terminal 104 and a negative terminal 106. The negative terminal 106 is connected to common wire 108, which connects the five groups G1-G5 of ultrasound radiating members 40 in series. The positive terminal 104 is connected to a plurality of lead wires 110, which each connect to one of the five groups G1-G5 of ultrasound radiating members 40. Thus, under this configuration, each of the five groups G1-G5, one of which is illustrated in FIG. 6, is connected to the positive terminal 104 via one of the lead wires 110, and to the negative terminal 106 via the common wire 108.

Referring now to FIG. 6, each group G1-G5 comprises a plurality of ultrasound radiating members 40. Each of the ultrasound radiating members 40 is electrically connected to the common wire 108 and to the lead wire 310 via one of two positive contact wires 112. Thus, when wired as illustrated, a constant voltage difference will be applied to each ultrasound radiating member 40 in the group. Although the group illustrated in FIG. 6 comprises twelve ultrasound radiating members 40, one of ordinary skill in the art will recognize that more or fewer ultrasound radiating members 40 can be included in the group. Likewise, more or fewer than five groups can be included within the ultrasound assembly 42 illustrated in FIG. 5.

Figure 7A:
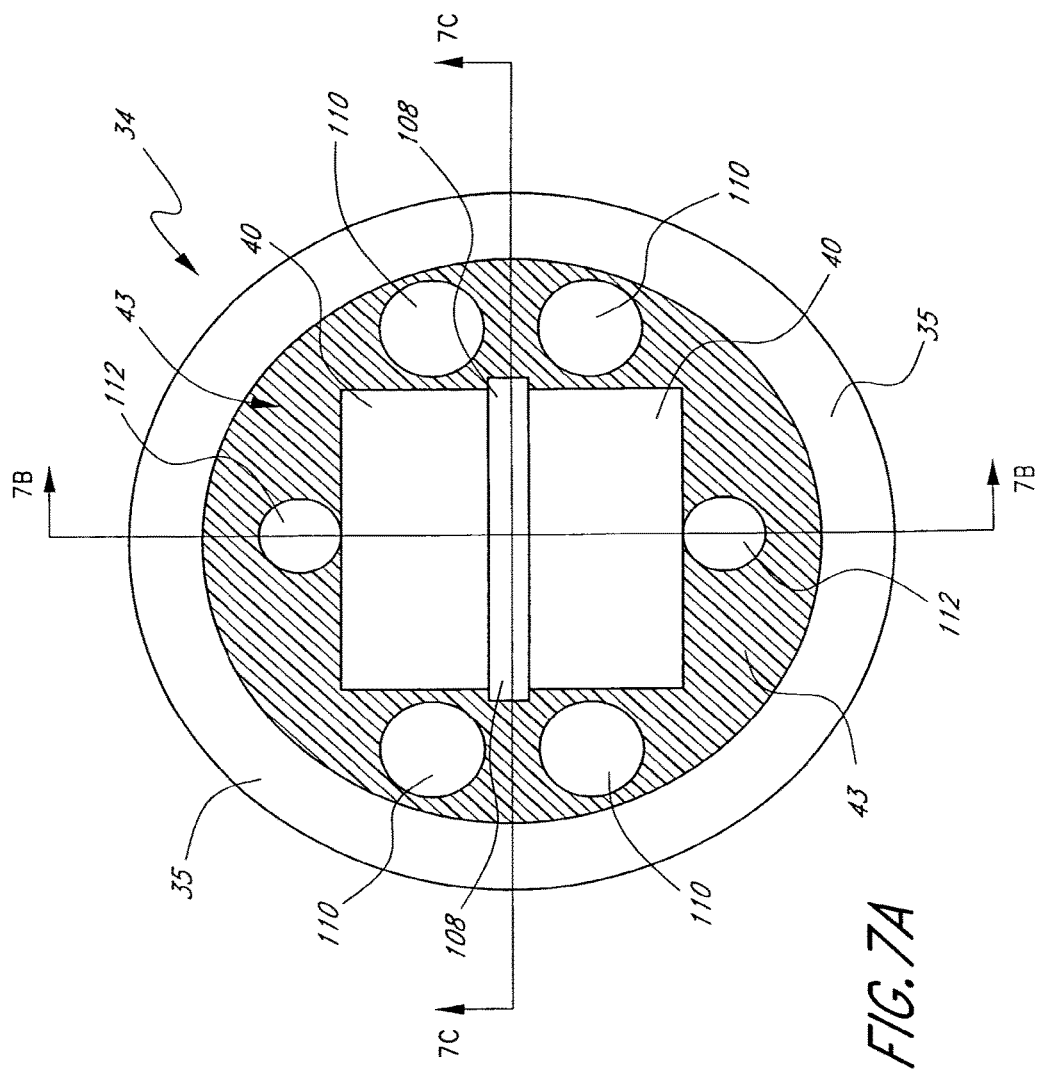
FIG. 7A is a schematic illustration of the ultrasound assembly of FIG. 5 housed within the inner core of FIG. 4.

FIG. 7A illustrates one preferred technique for arranging the components of the ultrasound assembly 42 (as schematically illustrated in FIG. 5) into the inner core 34 (as schematically illustrated in FIG. 4). FIG. 7A is a cross-sectional view of the ultrasound assembly 42 taken within group G1 in FIG. 5, as indicated by the presence of four lead wires 110. For example, if a cross-sectional view of the ultrasound assembly 42 was taken within group G4 in FIG. 5, only one lead wire 310 would be present (that is, the one lead wire connecting group G5).

Referring still to FIG. 7A, the common wire 108 comprises an elongate, flat piece of electrically conductive material in electrical contact with a pair of ultrasound radiating members 40. Each of the ultrasound radiating members 40 is also in electrical contact with a positive contact wire 312. Because the common wire 108 is connected to the negative terminal 106, and the positive contact wire 312 is connected to the positive terminal 104, a voltage difference can be created across each ultrasound radiating member 40. Lead wires 110 are preferably separated from the other components of the ultrasound assembly 42, thus preventing interference with the operation of the ultrasound radiating members 40 as described above. For example, in one preferred embodiment, the inner core 34 is filled with an insulating potting material 43, thus deterring unwanted electrical contact between the various components of the ultrasound assembly 42.

Figure 7B:
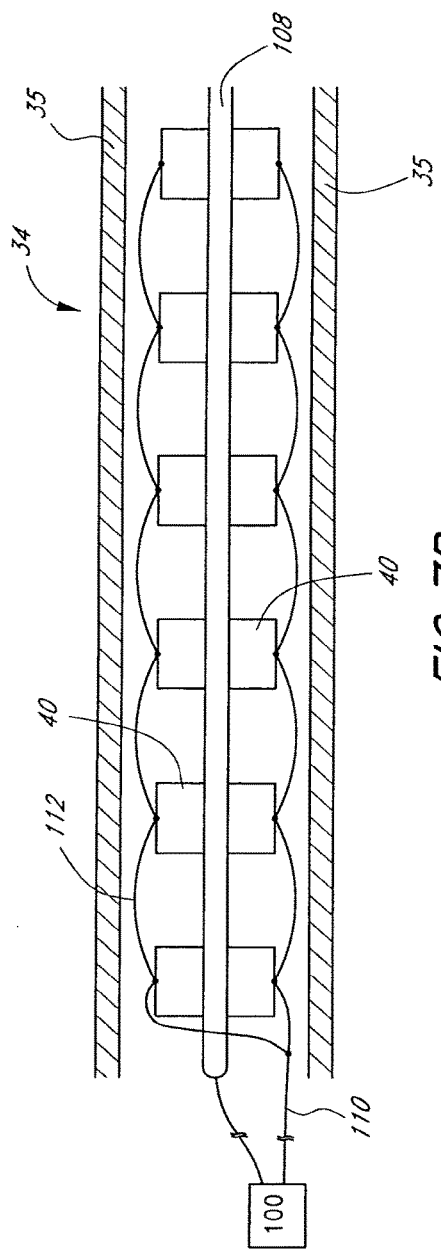
FIG. 7B is a cross-sectional view of the ultrasound assembly of FIG. 7A taken along line 7B-7B.
Figure 7C:
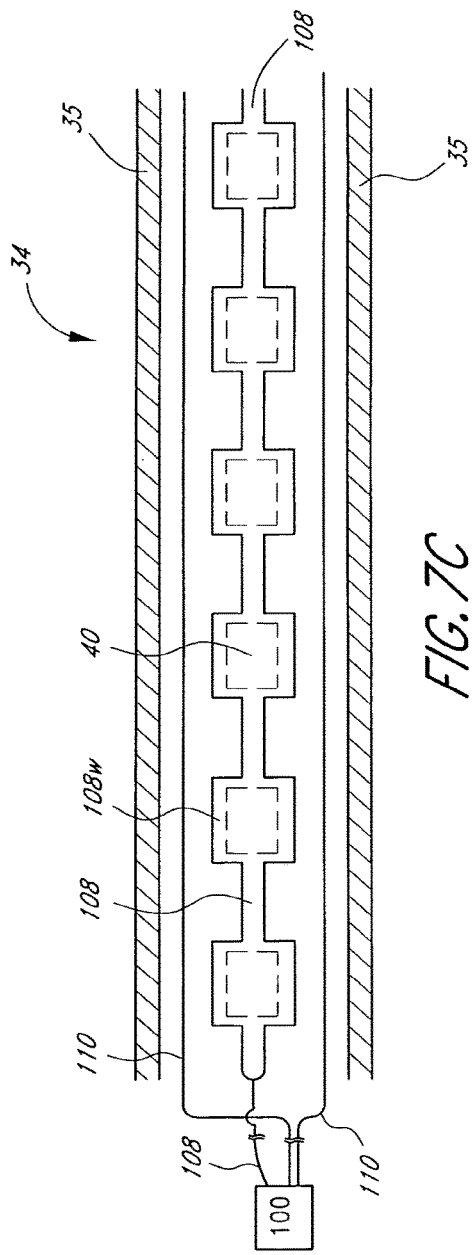
FIG. 7C is a cross-sectional view of the ultrasound assembly of FIG. 7A taken along line 7C-7C.

FIGS. 7B and 7C illustrate cross sectional views of the inner core 34 of FIG. 7A taken along lines 7B-7B and 7C-7C, respectively. As illustrated in FIG. 7B, the ultrasound radiating members 40 are mounted in pairs along the common wire 108. The ultrasound radiating members 40 are connected by positive contact wires 112, such that substantially the same voltage is applied to each ultrasound radiating member 40. As illustrated in FIG. 7C, the common wire 108 preferably comprises wide regions 108W upon which the ultrasound radiating members 40 can be mounted, thus reducing the likelihood that the paired ultrasound radiating members 40 will short together. In certain embodiments, outside the wide regions 108W, the common wire 108 may have a more conventional, rounded wire shape.

Figure 7D:
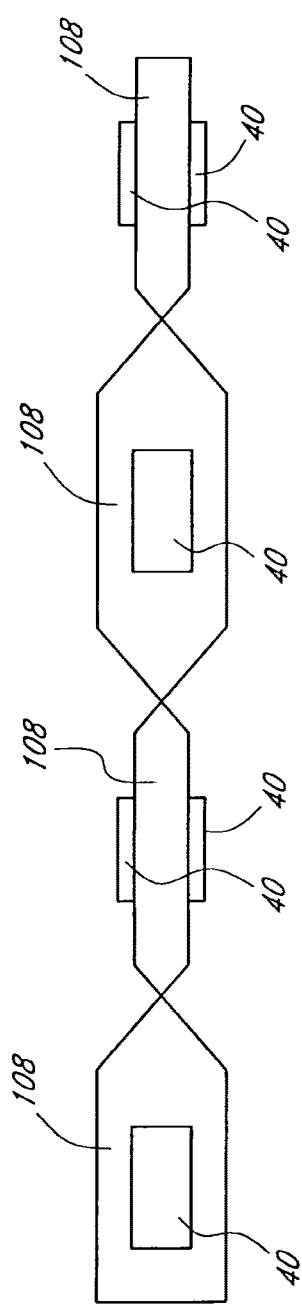
FIG. 7D is a side view of an ultrasound assembly center wire twisted into a helical configuration.

In a modified embodiment, such as illustrated in FIG. 7D, the common wire 108 is twisted to form a helical shape before being fixed within the inner core 34. In such embodiments, the ultrasound radiating members 40 are oriented in a plurality of radial directions, thus enhancing the radial uniformity of the resulting ultrasonic energy field.

One of ordinary skill in the art will recognize that the wiring arrangement described above can be modified to allow each group G1, G2, G3, G4, G5 to be independently powered. Specifically, by providing a separate power source within the control system 100 for each group, each group can be individually turned on or off, or can be driven with an individualized power. This provides the advantage of allowing the delivery of ultrasonic energy to be "turned off" in regions of the treatment site where treatment is complete, thus preventing deleterious or unnecessary ultrasonic energy to be applied to the patient.

The embodiments described above, and illustrated in FIGS. 5 through 7, illustrate a plurality of ultrasound radiating members grouped spatially. That is, in such embodiments, all of the ultrasound radiating members within a certain group are positioned adjacent to each other, such that when a single group is activated, ultrasonic energy is delivered at a specific length of the ultrasound assembly. However, in modified embodiments, the ultrasound radiating members of a certain group may be spaced apart from each other, such that the ultrasound radiating members within a certain group are not positioned adjacent to each other. In such embodiments, when a single group is activated, ultrasonic energy can be delivered from a larger, spaced apart portion of the energy delivery section. Such modified embodiments may be advantageous in applications wherein it is desired to deliver a less focussed, more diffuse ultrasonic energy field to the treatment site.

In a preferred embodiment, the ultrasound radiating members 40 comprise rectangular lead zirconate titanate ("PZT") ultrasound transducers that have dimensions of about 0.017 inches by about 0.010 inches by about 0.080 inches. In other embodiments, other configuration may be used. For example, disc-shaped ultrasound radiating members 40 can be used in other embodiments. In a preferred embodiment, the common wire 108 comprises copper, and is about 0.005 inches thick, although other electrically conductive materials and other dimensions can be used in other embodiments. Lead wires 110 are preferably 36 gauge electrical conductors, while positive contact wires 112 are preferably 42 gauge electrical conductors. However, one of ordinary skill in the art will recognize that other wire gauges can be used in other embodiments.

As described above, suitable frequencies for the ultrasound radiating member 40 include, but are not limited to, from about 20 kHz to about 20 MHz. In one embodiment, the frequency is between about 500 kHz and 20 MHz, and in another embodiment 1 MHz and 3 MHz. In yet another embodiment, the ultrasound radiating members 40 are operated with a frequency of about 2 MHz.

FIG. 8 illustrates the inner core 34 positioned within the tubular body 12. Details of the ultrasound assembly 42, provided in FIG. 7A, are omitted for clarity. As described above, the inner core 34 can be slid within the central lumen 51 of the tubular body 12, thereby allowing the inner core energy delivery section 41 to be positioned within the tubular body energy delivery section 18. For example, in a preferred embodiment, the materials comprising the inner core energy delivery section 41, the tubular body energy delivery section 18, and the potting material 43 all comprise materials having a similar acoustic impedance, thereby minimizing ultrasonic energy losses across material interfaces.

FIG. 8 further illustrates placement of fluid delivery ports 58 within the tubular body energy delivery section 18. As illustrated, holes or slits are formed from the fluid delivery lumen 30 through the tubular body 12, thereby permitting fluid flow from the fluid delivery lumen 30 to the treatment site. Thus, a source of therapeutic compound coupled to the inlet port 32 provides a hydraulic pressure which drives the therapeutic compound through the fluid delivery lumens 30 and out the fluid delivery ports 58.

By evenly spacing the fluid delivery lumens 30 around the circumference of the tubular body 12, as illustrated in FIG. 8, a substantially even flow of therapeutic compound around the circumference of the tubular body 12 can be achieved. In addition, the size, location and geometry of the fluid delivery ports 58 can be selected to provide uniform fluid flow from the fluid delivery ports 30 to the treatment site. For example, in one embodiment, fluid delivery ports closer to the proximal region of the energy delivery section 18 have smaller diameters then fluid delivery closer to the distal region of the energy delivery section 18, thereby allowing uniform delivery of fluid across the entire energy delivery section.

For example, in one embodiment in which the fluid delivery ports 58 have similar sizes along the length of the tubular body 12, the fluid delivery ports 58 have a diameter between about 0.0005 inches to about 0.0050 inches. In another embodiment in which the size of the fluid delivery ports 58 changes along the length of the tubular body 12, the fluid delivery ports 58 have a diameter between about 0.001 inches to about 0.005 inches in the proximal region of the energy delivery section 18, and between about 0.005 inches to 0.0020 inches in the distal region of the energy delivery section 18. The increase in size between adjacent fluid delivery ports 58 depends on the material comprising the tubular body 12, and on the size of the fluid delivery lumen 30. The fluid delivery ports 58 can be created in the tubular body 12 by punching, drilling, burning or ablating (such as with a laser), or by any other suitable method. Therapeutic compound flow along the length of the tubular body 12 can also be increased by increasing the density of the fluid delivery ports 58 toward the distal region 15 of the tubular body 12.

It should be appreciated that it may be desirable to provide non-uniform fluid flow from the fluid delivery ports 58 to the treatment site. In such embodiment, the size, location and geometry of the fluid delivery ports 58 can be selected to provide such non-uniform fluid flow.

Referring still to FIG. 8, placement of the inner core 34 within the tubular body 12 further defines cooling fluid lumens 44. Cooling fluid lumens 44 are formed between an outer surface 39 of the inner core 34 and an inner surface 16 of the tubular body 12. In certain embodiments, a cooling fluid can is introduced through the proximal access port 31 such that cooling fluid flow is produced through cooling fluid lumens 44 and out distal exit port 29 (see FIG. 1). The cooling fluid lumens 44 are preferably evenly spaced around the circumference of the tubular body 12 (that is, at approximately 120° increments for a three-lumen configuration), thereby providing uniform cooling fluid flow over the inner core 34. Such a configuration is desirably to remove unwanted thermal energy at the treatment site. As will be explained below, the flow rate of the cooling fluid and the power to the ultrasound assembly 42 can be adjusted to maintain the temp of the inner core energy delivery section 41 within a desired range.

In a preferred embodiment, the inner core 34 can be rotated or moved within the tubular body 12. Specifically, movement of the inner core 34 can be accomplished by maneuvering the proximal hub 37 while holding the backend hub 33 stationary. The inner core outer body 35 is at least partially constructed from a material that provides enough structural support to permit movement of the inner core 34 within the tubular body 12 without kinking of the tubular body 12. Additionally, the inner core outer body 35 preferably comprises a material having the ability to transmit torque. Suitable materials for the inner core outer body 35 include, but are not limited to, polyimides, polyesters, polyurethanes, thermoplastic elastomers and braided polyimides.

In a preferred embodiment, the fluid delivery lumens 30 and the cooling fluid lumens 44 are open at the distal end of the tubular body 12, thereby allowing the therapeutic compound and the cooling fluid to pass into the patient's vasculature at the distal exit port. Or, if desired, the fluid delivery lumens 30 can be selectively occluded at the distal end of the tubular body 12, thereby providing additional hydraulic pressure to drive the therapeutic compound out of the fluid delivery ports 58. In either configuration, the inner core 34 can prevented from passing through the distal exit port by making providing the inner core 34 with a length that is less than the length of the tubular body. In other embodiments, a protrusion is formed on the internal side of the tubular body in the distal region 15, thereby preventing the inner core 34 from passing through the distal exit port.

In still other embodiments, the catheter 10 further comprises an occlusion device (not shown) positioned at the distal exit port 29. The occlusion device preferably has a reduced inner diameter that can accommodate a guidewire, but that is less than the inner diameter of the central lumen 51. Thus, the inner core 34 is prevented from extending through the occlusion device and out the distal exit port 29. For example, suitable inner diameters for the occlusion device include, but are not limited to, about 0.005 inches to about 0.050 inches. In other embodiments, the occlusion device has a closed end, thus preventing cooling fluid from leaving the catheter 10, and instead recirculating to the proximal region 14 of the tubular body 12. These and other cooling fluid flow configurations permit the power provided to the ultrasound assembly 42 to be increased in proportion to the cooling fluid flow rate. Additionally, certain cooling fluid flow configurations can reduce exposure of the patient's body to cooling fluids.

In certain embodiments, as illustrated in FIG. 8, the tubular body 12 further comprises one or more temperature sensors 20, which are preferably located within the energy delivery section 18. In such embodiments, the proximal region 14 of the tubular body 12 includes a temperature sensor lead which can be incorporated into cable 45 (illustrated in FIG. 1). Suitable temperature sensors include, but are not limited to, temperature sensing diodes, thermistors, thermocouples, resistance temperature detectors ("RTDs") and fiber optic temperature sensors which use thermalchromic liquid crystals. Suitable temperature sensor 20 geometries include, but are not limited to, a point, a patch or a stripe. The temperature sensors 20 can be positioned within one or more of the fluid delivery lumens 30 (as illustrated), and/or within one or more of the cooling fluid lumens 44.

Figure 9:
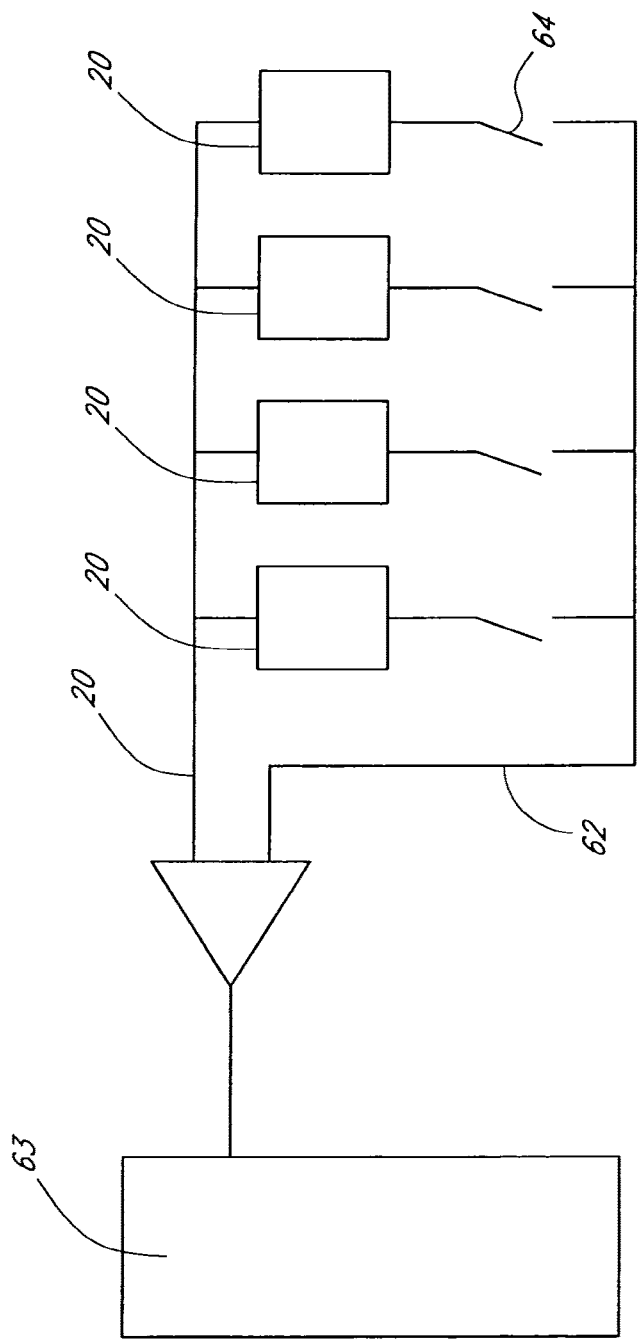
FIG. 9 illustrates a wiring diagram for connecting a plurality of temperature sensors with a common wire.

FIG. 9 illustrates one embodiment for electrically connecting the temperature sensors 20. In such embodiments, each temperature sensor 20 is coupled to a common wire 61 and is associated with an individual return wire 62. Accordingly, n+1 wires can be used to independently sense the temperature at n distinct temperature sensors 20. The temperature at a particular temperature sensor 20 can be determined by closing a switch 64 to complete a circuit between that thermocouple's individual return wire 62 and the common wire 61. In embodiments wherein the temperature sensors 20 comprise thermocouples, the temperature can be calculated from the voltage in the circuit using, for example, a sensing circuit 63, which can be located within the external control circuitry 100.

In other embodiments, each temperature sensor 20 is independently wired. In such embodiments, 2n wires through the tubular body 12 to independently sense the temperature at n independent temperature sensors 20. In still other embodiments, the flexibility of the tubular body 12 can be improved by using fiber optic based temperature sensors 20. In such embodiments, flexibility can be improved because only n fiber optic members are used to sense the temperature at n independent temperature sensors 20.

Figure 10:
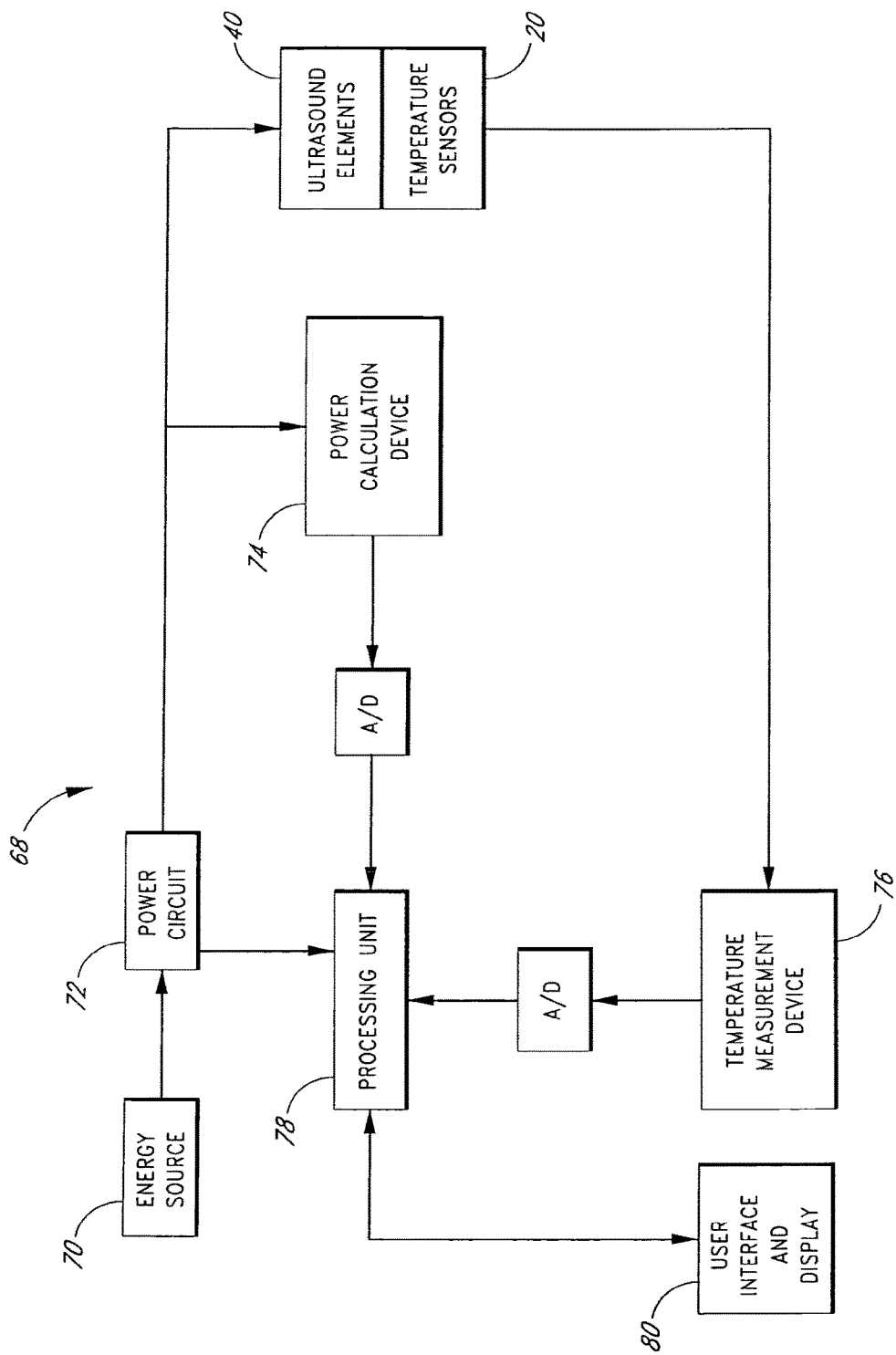
FIG. 10 is a block diagram of a feedback control system for use with an ultrasonic catheter.

FIG. 10 illustrates one embodiment of a feedback control system 68 that can be used with the catheter 10. The feedback control system 68 can be integrated into the control system that is connected to the inner core 34 via cable 45 (as illustrated in FIG. 1). The feedback control system 68 allows the temperature at each temperature sensor 20 to be monitored and allows the output power of the energy source 70 to be adjusted accordingly. A physician can, if desired, override the closed or open loop system.

The feedback control system 68 preferably comprises an energy source 70, power circuits 72 and a power calculation device 74 that is coupled to the ultrasound radiating members 40. A temperature measurement device 76 is coupled to the temperature sensors 20 in the tubular body 12. A processing unit 78 is coupled to the power calculation device 74, the power circuits 72 and a user interface and display 80.

In operation, the temperature at each temperature sensor 20 is determined by the temperature measurement device 76. The processing unit 78 receives each determined temperature from the temperature measurement device 76. The determined temperature can then be displayed to the user at the user interface and display 80.

The processing unit 78 comprises logic for generating a temperature control signal. The temperature control signal is proportional to the difference between the measured temperature and a desired temperature. The desired temperature can be determined by the user (at set at the user interface and display 80) or can be preset within the processing unit 78.

The temperature control signal is received by the power circuits 72. The power circuits 72 are preferably configured to adjust the power level, voltage, phase and/or current of the electrical energy supplied to the ultrasound radiating members 40 from the energy source 70. For example, when the temperature control signal is above a particular level, the power supplied to a particular group of ultrasound radiating members 40 is preferably reduced in response to that temperature control signal. Similarly, when the temperature control signal is below a particular level, the power supplied to a particular group of ultrasound radiating members 40 is preferably increased in response to that temperature control signal. After each power adjustment, the processing unit 78 preferably monitors the temperature sensors 20 and produces another temperature control signal which is received by the power circuits 72.

The processing unit 78 preferably further comprises safety control logic. The safety control logic detects when the temperature at a temperature sensor 20 has exceeded a safety threshold. The processing unit 78 can then provide a temperature control signal which causes the power circuits 72 to stop the delivery of energy from the energy source 70 to that particular group of ultrasound radiating members 40.

Because, in certain embodiments, the ultrasound radiating members 40 are mobile relative to the temperature sensors 20, it can be unclear which group of ultrasound radiating members 40 should have a power, voltage, phase and/or current level adjustment. Consequently, each group of ultrasound radiating member 40 can be identically adjusted in certain embodiments. In a modified embodiment, the power, voltage, phase, and/or current supplied to each group of ultrasound radiating members 40 is adjusted in response to the temperature sensor 20 which indicates the highest temperature. Making voltage, phase and/or current adjustments in response to the temperature sensed by the temperature sensor 20 indicating the highest temperature can reduce overheating of the treatment site.

The processing unit 78 also receives a power signal from a power calculation device 74. The power signal can be used to determine the power being received by each group of ultrasound radiating members 40. The determined power can then be displayed to the user on the user interface and display 80.

As described above, the feedback control system 68 can be configured to maintain tissue adjacent to the energy delivery section 18 below a desired temperature. For example, it is generally desirable to prevent tissue at a treatment site from increasing more than 6° C. As described above, the ultrasound radiating members 40 can be electrically connected such that each group of ultrasound radiating members 40 generates an independent output. In certain embodiments, the output from the power circuit maintains a selected energy for each group of ultrasound radiating members 40 for a selected length of time.

The processing unit 78 can comprise a digital or analog controller, such as for example a computer with software. When the processing unit 78 is a computer it can include a central processing unit ("CPU") coupled through a system bus. As is well known in the art, the user interface and display 80 can comprise a mouse, a keyboard, a disk drive, a display monitor, a nonvolatile memory system, or any another. Also preferably coupled to the bus is a program memory and a data memory.

In lieu of the series of power adjustments described above, a profile of the power to be delivered to each group of ultrasound radiating members 40 can be incorporated into the processing unit 78, such that a preset amount of ultrasonic energy to be delivered is pre-profiled. In such embodiments, the power delivered to each group of ultrasound radiating members 40 can then be adjusted according to the preset profiles.

The ultrasound radiating members are preferably operated in a pulsed mode. For example, in one embodiment, the time average power supplied to the ultrasound radiating members is preferably between about 0.1 watts and 2 watts and more preferably between about 0.5 watts and 1.5 watts. In certain preferred embodiments, the time average power is approximately 0.6 watts or 1.2 watts. The duty cycle is preferably between about 1% and 50% and more preferably between about 5% and 25%. In certain preferred embodiments, the duty ratio is approximately 7.5% or 15%. The pulse averaged power is preferably between about 0.1 watts and 20 watts and more preferably between approximately 5 watts and 20 watts. In certain preferred embodiments, the pulse averaged power is approximately 8 watts and 16 watts. The amplitude during each pulse can be constant or varied.

In one embodiment, the pulse repetition rate is preferably between about 5 Hz and 150 Hz and more preferably between about 10 Hz and 50 Hz. In certain preferred embodiments, the pulse repetition rate is approximately 30 Hz. The pulse duration is preferably between about 1 millisecond and 50 milliseconds and more preferably between about 1 millisecond and 25 milliseconds. In certain preferred embodiments, the pulse duration is approximately 2.5 milliseconds or 5 milliseconds.

In one particular embodiment, the transducers are operated at an average power of approximately 0.6 watts, a duty cycle of approximately 7.5%, a pulse repetition rate of 30 Hz, a pulse average electrical power of approximately 8 watts and a pulse duration of approximately 2.5 milliseconds.

The ultrasound radiating member used with the electrical parameters described herein preferably has an acoustic efficiency greater than 50% and more preferably greater than 75%. The ultrasound radiating member can be formed a variety of shapes, such as, cylindrical (solid or hollow), flat, bar, triangular, and the like. The length of the ultrasound radiating member is preferably between about 0.1 cm and about 0.5 cm. The thickness or diameter of the ultrasound radiating members is preferably between about 0.02 cm and about 0.2 cm.

Figure 11A:
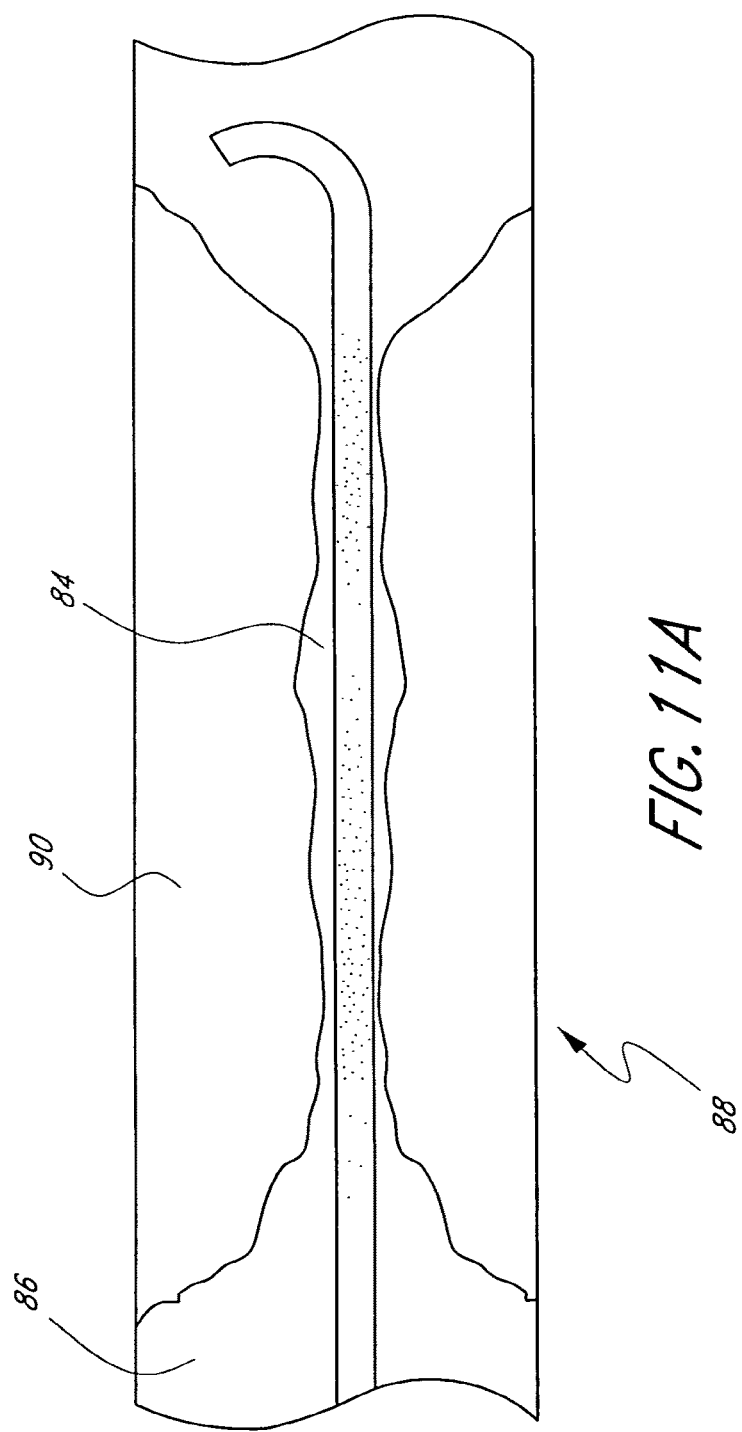
FIG. 11A is a side view of a treatment site.
Figure 11D:
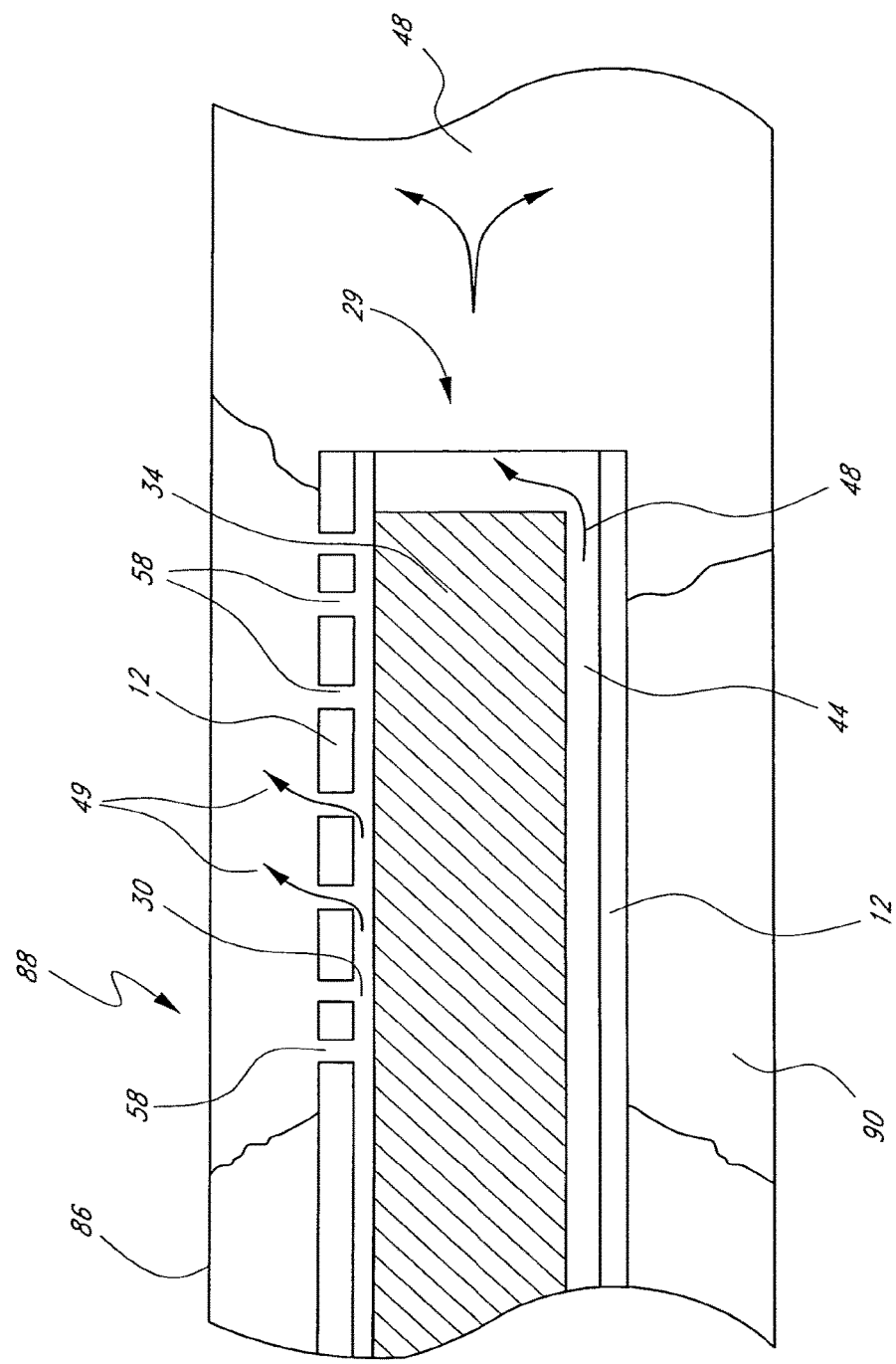
FIG. 11D is a cross-sectional view of the distal end of the ultrasonic catheter of FIG. 11C, wherein an inner core has been inserted into the tubular body to perform a treatment.

FIGS. 11A through 11D illustrate a method for using the ultrasonic catheter 10. As illustrated in FIG. 11A, a guidewire 84 similar to a guidewire used in typical angioplasty procedures is directed through a patient's vessels 86 to a treatment site 88 which includes a clot 90. The guidewire 84 is directed through the clot 90. Suitable vessels 86 include, but are not limited to, the large periphery blood vessels of the body. Additionally, as mentioned above, the ultrasonic catheter 10 also has utility in various imaging applications or in applications for treating and/or diagnosing other diseases in other body parts.

As illustrated in FIG. 10B, the tubular body 12 is slid over and is advanced along the guidewire 84 using conventional over-the-guidewire techniques. The tubular body 12 is advanced until the energy delivery section 18 of the tubular body 12 is positioned at the clot 90. In certain embodiments, radiopaque markers (not shown) are positioned along the energy delivery section 18 of the tubular body 12 to aid in the positioning of the tubular body 12 within the treatment site 88.

As illustrated in FIG. 10C, the guidewire 84 is then withdrawn from the tubular body 12 by pulling the guidewire 84 from the proximal region 14 of the catheter 10 while holding the tubular body 12 stationary. This leaves the tubular body 12 positioned at the treatment site 88.

As illustrated in FIG. 10D, the inner core 34 is then inserted into the tubular body 12 until the ultrasound assembly 42 abuts against the occlusion device and is positioned at least partially within the energy delivery section 18 of the tubular body 12. Once the inner core 34 is properly positioned, the ultrasound assembly 42 is activated to deliver ultrasonic energy through the energy delivery section 18 to the clot 90. As described above, suitable ultrasonic energy is delivered with a frequency between about 20 kHz and about 20 MHz.

In a certain embodiment, the ultrasound assembly 42 comprises sixty ultrasound radiating members 40 spaced over a length of approximately 30 to 50 cm. In such embodiments, the catheter 10 can be used to treat an elongate clot 90 without requiring movement of or repositioning of the catheter 10 during the treatment. However, it will be appreciated that in modified embodiments the inner core 34 can be moved or rotated within the tubular body 12 during the treatment. Such movement can be accomplished by maneuvering the proximal hub 37 of the inner core 34 while holding the backend hub 33 stationary.

Referring again to FIG. 11D, arrows 48 indicate that a cooling fluid flows through the cooling fluid lumen 44 and out the distal exit port 29. Likewise, arrows 49 indicated that a therapeutic compound flows through the fluid delivery lumen 30 and out the fluid delivery ports 58 to the treatment site 88.

The cooling fluid can be delivered before, after, during or intermittently with the delivery of ultrasonic energy. Similarly, the therapeutic compound can be delivered before, after, during or intermittently with the delivery of ultrasonic energy. Consequently, the steps illustrated in FIGS. 11A through 11D can be performed in a variety of different orders than that described above. The therapeutic compound and ultrasonic energy are preferably applied until the clot 90 is partially or entirely dissolved. Once the clot 90 has been dissolved to the desired degree, the tubular body 12 and the inner core 34 are withdrawn from the treatment site 88.

Figure 12:
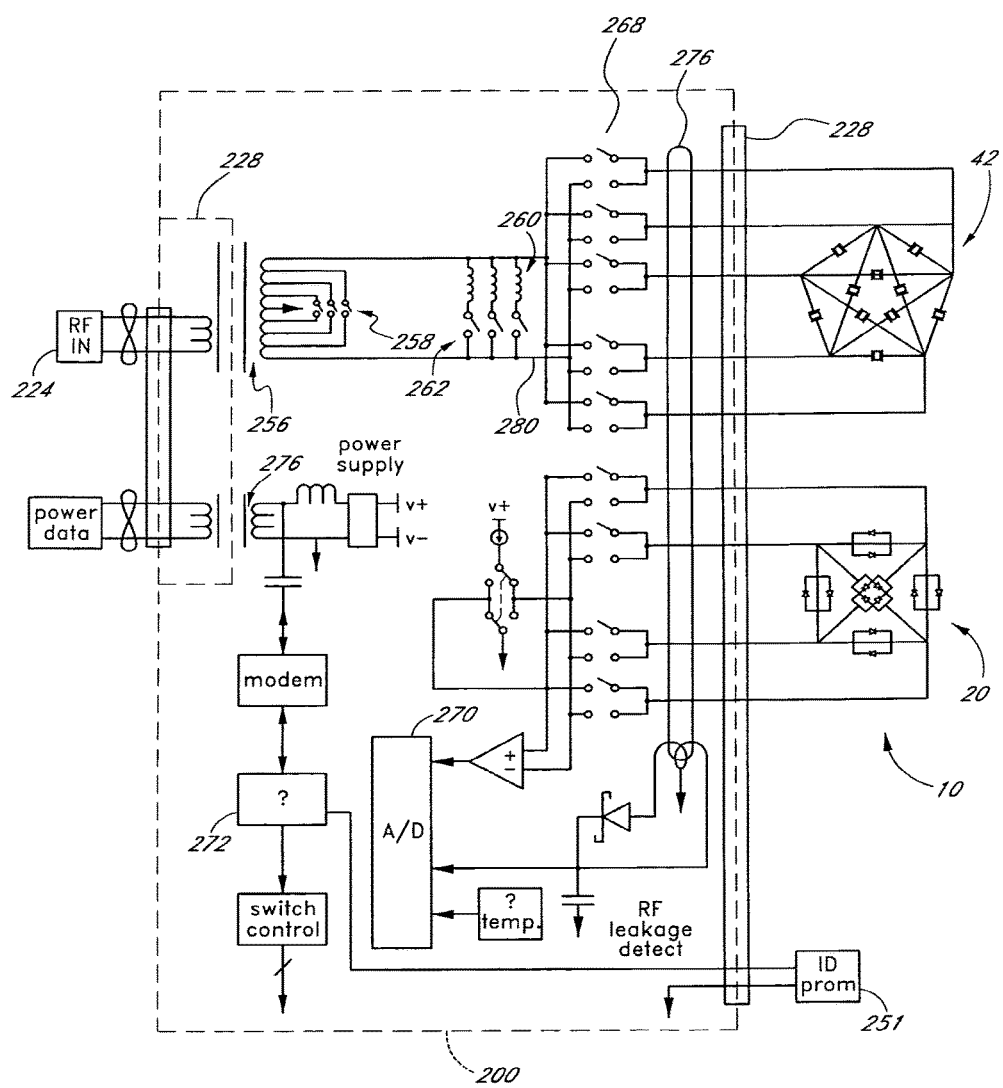
FIG. 12 is a circuit diagram of an isolation pod.

To reduce electric current leakage through the patient's body to ground, in certain embodiments the control system 100 may comprise an isolation pod 200. FIG. 12 illustrates one embodiment of an isolation pod 200 that is contains certain portions of the control system 100, as described in more detail below. Preferably, the external control circuitry 100, including the isolation pod 200 (if any), is positioned proximal to the backend hub 33 (see FIG. 1), thereby preventing crosstalk between the wiring to the plurality of groups of ultrasound radiating members.

The isolation pod 200 comprises an isolation barrier 228 configured to reduce or eliminate unwanted electrical current flow through the patient's body. For example, in the illustrated embodiment, two transformers 256, 276 form an isolation barrier between the external control circuitry 100 and the certain components of the isolation pod 200.

Referring still to FIG. 12, a transformer loop 278 is used to measure the leakage current of the catheter 10. This leakage current represents the current that does not return to the isolation pod 200 through the return lines, but instead passes through the patient's body to ground. A center tap from the transformer loop 278 connects to two diodes that rectify the leakage current. In this example, zener diodes with a low threshold voltage are used to rectify the small signal provided from the transformer loop.

The external control circuitry 100 provides a radio frequency signal 224 for driving the ultrasound assembly 42. The radio frequency signal 224 operates in the ultrasonic frequency range, and is tuned to a frequency that activates the ultrasound radiating members 40 in the inner core 34. The radio frequency signal 224 is electromagnetically coupled to the isolation pod 200 using a transformer 256. The dielectric layers of the transformer 256 form an isolation barrier. This isolation barrier substantially prevents electrical current from flowing from the isolation pod 200, through the patient's body, and back into the isolation pod 200. By electromagnetically coupling the driving radio frequency signal to the isolation pod 200, the current loop is broken and electric current is thereby prevented from flowing through the patient's body.

In the embodiment illustrated in FIG. 12, the isolation pod 200 is compatible with multiple types of catheters. The different catheters can use different types or quantities of ultrasound radiating members, which in turn may cause variations in the input impedance seen by the radio frequency amplifier. Even if the ultrasound radiating members are configured to be identical, fabrication defects will often cause the impedance of ultrasound radiating members to vary. Additionally, the activation pattern or configuration of ultrasound radiating members within a catheter can also alter the input impedance.

The exemplary isolation pod 200 includes circuitry to enable matching the output impedance of the radio frequency amplifier to the input impedance of the ultrasound radiating members. For example, many radio frequency amplifiers have an output impedance of about 50Ω. To maximize power efficiency, the isolation pod 200 attempts to match the impedance by providing a substantially equivalent 50Ω at the input.

Still referring to FIG. 12, the isolation pod 200 provides circuitry for tuning the input impedance of the isolation pod 200 to match the output impedance of the radio frequency amplifier. For example, FIG. 12 illustrates the coupling transformer 256 with taps 258 on the secondary side. Selecting different taps modifies the turns ratio of the transformer and thereby changes the input impedance of the isolation pod 200.

Changing the turns ratio of the coupling transformer 256 also affects the amplitude of the current passing through the ultrasonic assembly 42. As needed, the external control circuitry 100 compensates for these changes in amplitude for example by driving the radio frequency signal at different levels.

The embodiment illustrated in FIG. 12 also shows the use of inductors 260 for tuning the input impedance. As illustrated, the isolation pod 200 further comprises three individually controlled switches 262 that connect the three inductors with the radio frequency input circuit. In this example, a total of eight tuning settings are achievable by opening and closing the inductor switches in various combinations. The tuning circuitry is not limited to the use of inductors or transformer taps. Other components, such as capacitors and resistors, may also be used to tune the input impedance.

In one embodiment, tuning information is determined for a catheter at the time of manufacture. The tuning information is then embedded into the catheter, such as by saving the tuning information in an identification programmable read-only memory ("PROM") 254. Alternatively, the serial number or other identifying indicia of the catheter together with the tuning information is entered into a database. The isolation pod 200 then retrieves the tuning information from the database and appropriately adjusts the tuning circuitry to the catheter that is attached to the isolation pod 200.

In another embodiment, the isolation pod 200 includes internal circuitry to detect the impedance of the ultrasound assembly 42 in the catheter and adjusts the tuning circuitry appropriately.

FIG. 12 further illustrates a configuration that is particularly adapted for the use of multiple ultrasound radiating members such as in the arrangements described above. In the illustrated embodiment, ten ultrasound radiating members are connected to the isolation pod 200 using five connections. The ultrasound radiating members are controlled by multiplexing the driving signal through five pairs of switches 268. The ultrasound radiating member driving lines in the inner core 34 connect to the pairs of switches 268 within the isolation pod 200. Each pair of switches 268 has four settings: (open, open), (open, closed), (closed, open) and (closed, closed). In operation, only three settings are used because the (closed, closed) setting short-circuits the driving signal. In the illustrated example, wherein there are five ultrasound radiating member driving lines, $3^5=243$ modes of operation are available. Examples of these modes are described in the embodiments that follow.

Figure 13:
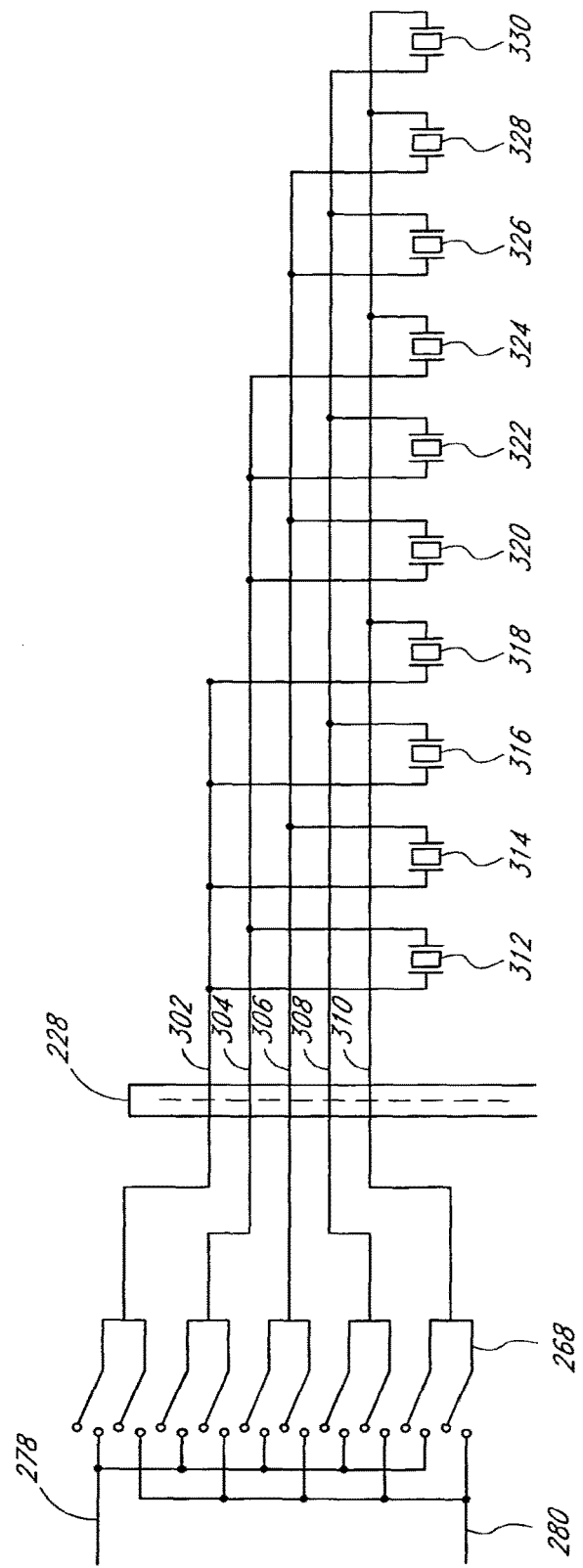
FIG. 13 illustrates the connection of ultrasound radiating members within a catheter to an isolation pod.

FIG. 13 illustrates an arrangement where the ultrasound radiating members are linearly spaced within the catheter. In the illustrated example, the catheter has five ultrasound radiating member driving lines 302, 304, 306, 308, and 310.

In one embodiment, one pair of switches is in the (closed, open) setting and the remaining four pairs of switches are in the (open, closed) setting. In this such embodiments, four ultrasound radiating members are active at a time. The remaining six ultrasound radiating members have both terminals short circuited, so they are not active.

Figure 14:
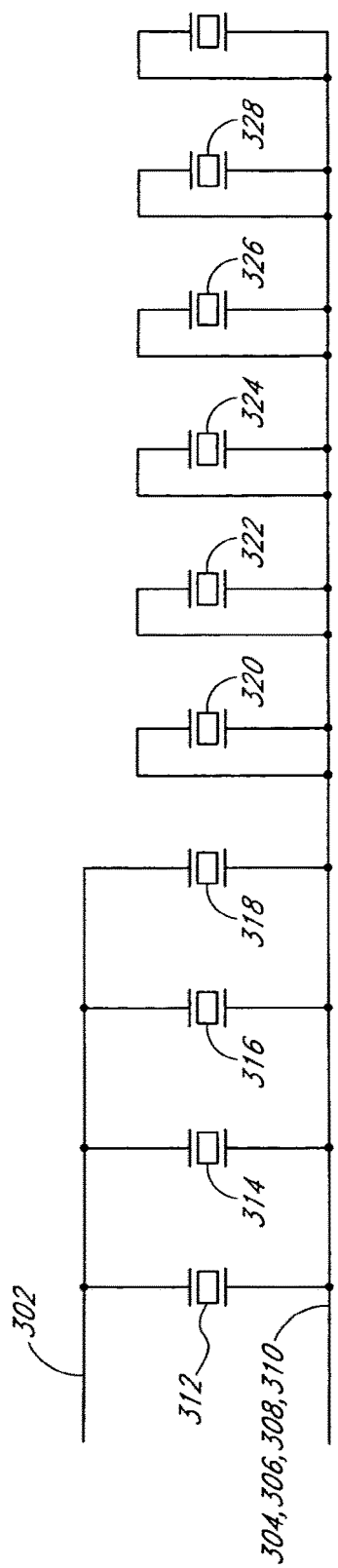
FIG. 14 illustrates a selective activation of ultrasound radiating members within a catheter.

FIG. 14 illustrates an embodiment wherein the pair of switches for the first ultrasound radiating member driving line 302 is in the (closed, open) setting and the pairs of switches for the remaining ultrasound radiating member driving lines 304, 306, 308, 310 are in the (open, closed) setting. In this configuration, four ultrasound radiating members 312, 314, 316, 318 are active, and six remaining ultrasound radiating members 320, 322, 324, 326, 328, 330 are inactive. The active ultrasound radiating members 312, 314, 316, 318 have substantially the same voltage differential appearing across the ultrasound radiating members terminals.

Figure 15:
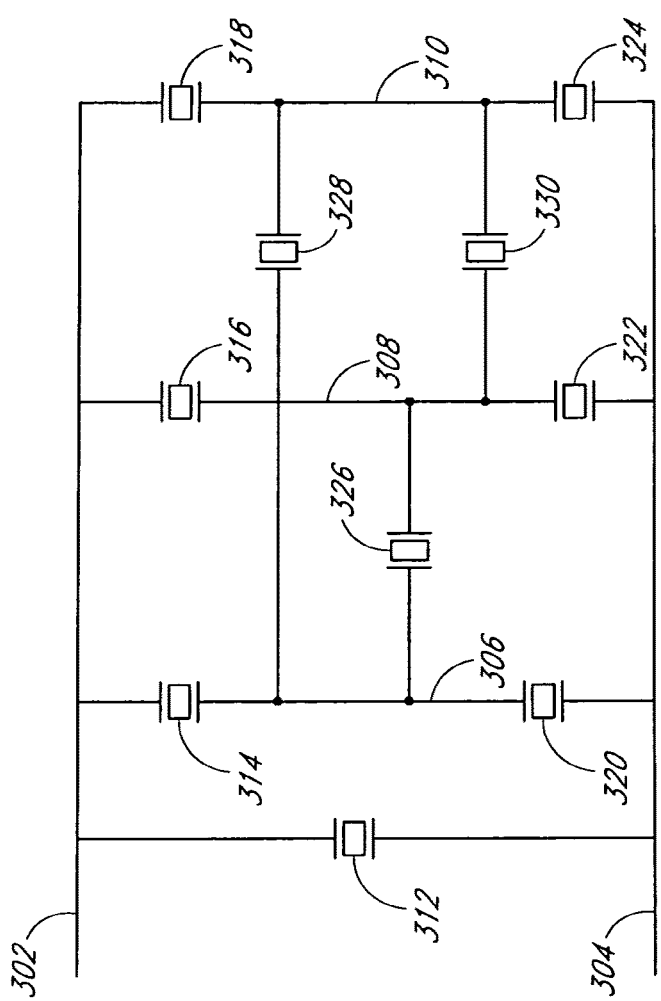
FIG. 15 illustrates a second selective activation of ultrasound radiating members within a catheter.

FIG. 15 illustrates an embodiment wherein one pair of switches is in the (closed, open) setting and another pair of switches is in the (open, closed) setting. As illustrated, the pair of switches for the first ultrasound radiating member driving line 302 is in the (closed, open) setting, the pair of switches for the second ultrasound radiating member driving line 304 is in the (open, closed) setting, and the pairs of switches for the remaining ultrasound radiating member driving lines 306, 308, 310 are in the (open, open) setting. The resulting network of connections between the ultrasound radiating member form several voltage dividers. This results in different voltage differences across the terminals of the various ultrasound radiating members. Assuming the ultrasound radiating members are equivalent, the first ultrasound radiating member 312 will have the full driving signal appearing across its terminals, six ultrasound radiating members 314, 316, 318, 320, 322, 324 will have a half-strength driving signal appearing across their terminals, and the remaining three ultrasound radiating members 326, 328, 330 will have no voltage differential appearing across their terminals.

Figure 16:
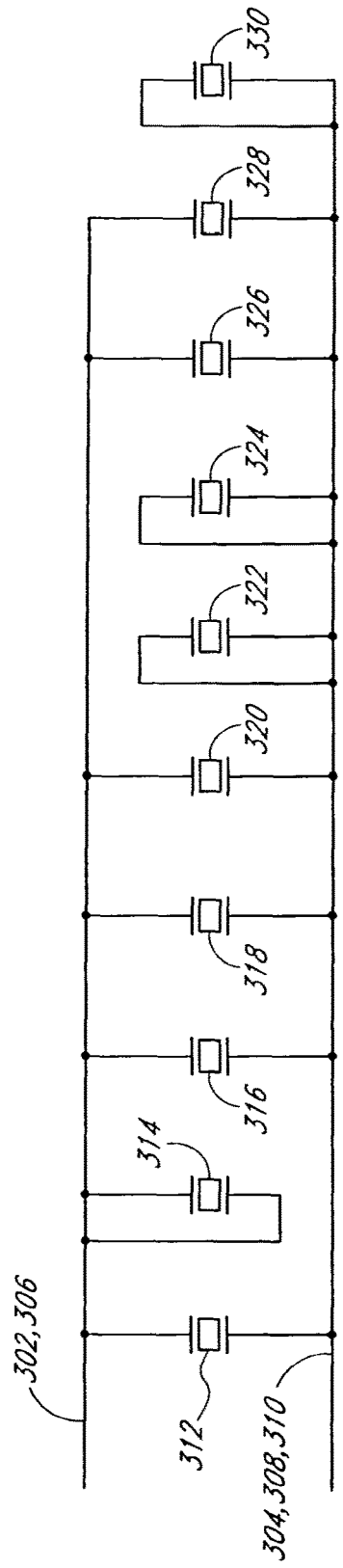
FIG. 16 illustrates a third selective activation of ultrasound radiating members within a catheter.

FIG. 16 illustrates an embodiment wherein the pairs of switches for the first and third ultrasound radiating member driving lines 302, 306 are in the (closed, open) setting and the pairs of switches for the remaining ultrasound radiating member driving lines 304, 308, 310 are in the (open, closed) setting. In this configuration, six ultrasound radiating members 312, 316, 318, 320, 326, 328 are active, and the remaining four ultrasound radiating members 314, 322, 324, 330 are inactive.

Figure 17:
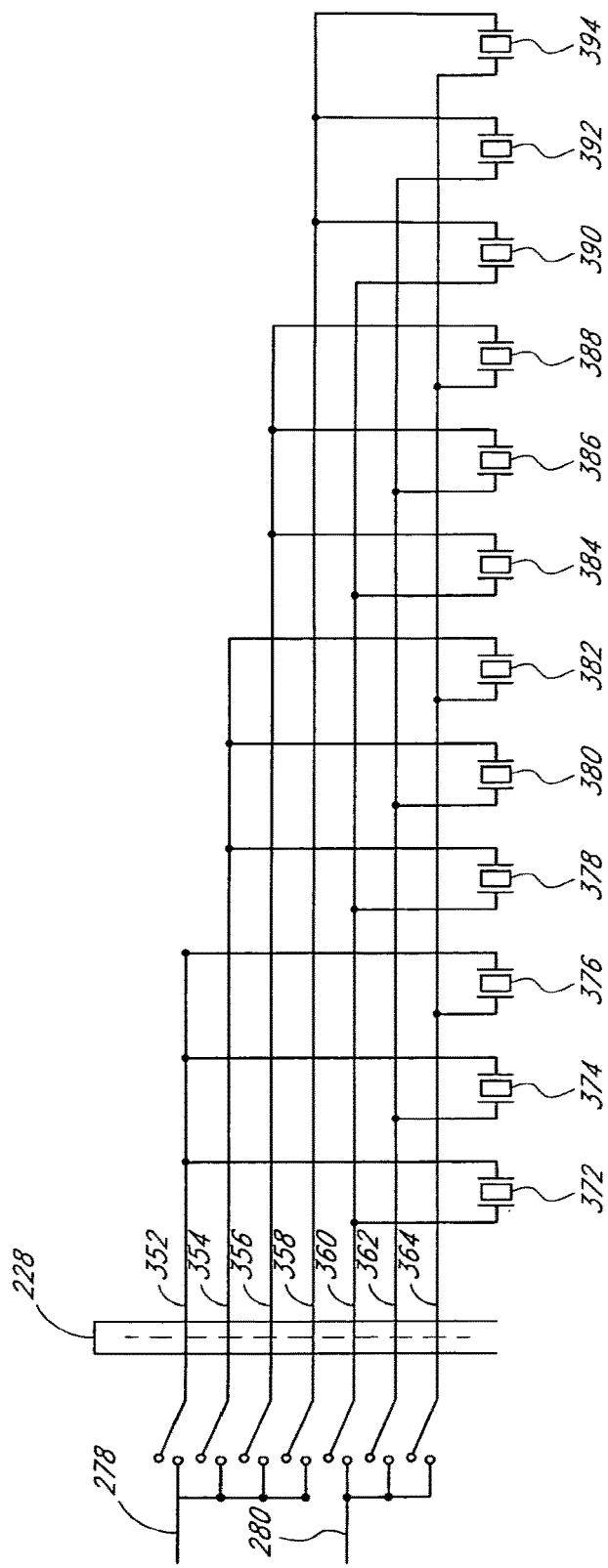
FIG. 17 illustrates one embodiment for connecting ultrasound radiating members within a catheter to an isolation pod.

FIG. 17 shows a modified catheter configuration with seven connections to the isolation pod 200. In such a configuration, the isolation pod 200 uses four switches to connect the first terminal 278 of the driving signal to the first four ultrasound radiating member driving lines 352, 354, 356, 358, and three switches to connect the second terminal 280 of the driving signal to the remaining three ultrasound radiating member driving lines 360, 362, 364. When all of the switches connected to the first terminal 278 are in the (closed) setting, each switch connected to the second terminal 280 activates a bank of four ultrasound radiating members. For example, if all the switches to the first terminal 278 are closed, closing the switch for the ultrasound radiating member driving line 360 activates four ultrasound radiating members 372, 378, 384, 390. Closing the switch for the ultrasound radiating member driving line 362 activates four ultrasound radiating members 374, 380, 386, 392, and closing the switch for the ultrasound radiating member driving line 364 activates four ultrasound radiating members 376, 382, 388, 394. The banks are independently operable, so zero, one or two banks can be active at any given time.

Alternatively, when all of the switches connected to the second terminal 280 are in the (closed) setting, each switch connected to the first terminal 278 activates a bank of three ultrasound radiating members. For example, if all the switches to the second terminal 280 are closed, closing the switch for the ultrasound radiating member driving line 352 activates three ultrasound radiating members 372, 374, 376, 378. Other banks of three ultrasound radiating members are activated by the closing switches for the remaining three ultrasound radiating member driving lines 354, 356, 358. Again, the banks are independently operable, so zero, one, two, or three banks can be active at any given time.

It is not necessary to activate the ultrasound radiating members in banks, because the switches can be individually controlled. A total of $2^7=128$ driving combinations are possible. The non-bank configurations include voltage divider circuits, so all of the ultrasound radiating members are not driven at full strength in these configurations.

Figure 18:
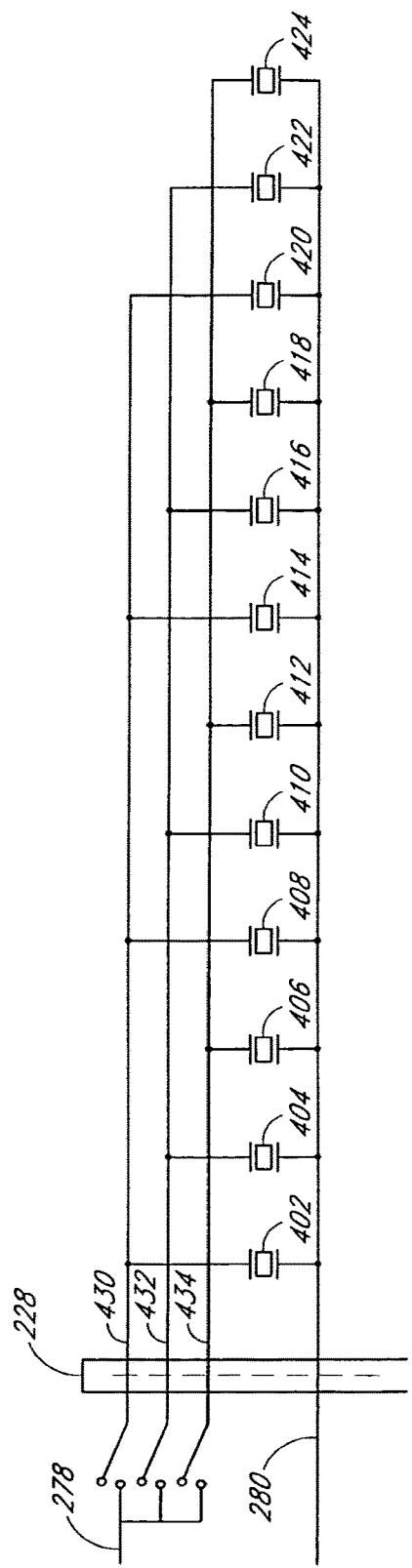
FIG. 18 illustrates a second embodiment for connecting ultrasound radiating members within a catheter to an isolation pod.

FIG. 18 illustrates another catheter embodiment where the ultrasound radiating members are arranged in three banks with four ultrasound radiating members in each bank. Closing the switch for ultrasound radiating member driving line 430 activates four ultrasound radiating members 402, 408, 414, 420. Closing the switch for ultrasound radiating member driving line 432 activates four ultrasound radiating members 404, 410, 416, 422. Closing the switch for ultrasound radiating member driving line 434 activates four ultrasound radiating members 406, 412, 418, 424.

One of ordinary skill in the art will understand that the illustrated embodiments are exemplary and that the catheter design is not limited to the illustrated configurations. For example, the catheter may include different numbers of ultrasound radiating members, ultrasound radiating member driving lines, or switches. Some or all of the switches may alternately be included as part of the catheter.

A catheter may include ultrasound radiating members tuned to resonate at multiple frequencies. Ultrasound radiating members having the same resonant frequency can be selected individually or in groups. Alternatively, ultrasound radiating members having different resonant frequencies can be driven by the same driving signal. In such embodiments, the amount of ultrasonic energy delivered by an ultrasound radiating member depends in part on the frequency at which the ultrasound radiating member is driven.

Controlling the amplitude and frequency of the driving signal and arranging the placement of the ultrasound radiating members allows the catheter to deliver appropriate ultrasonic energy levels to the treatment site. In certain applications, it is desired that the catheter delivers a uniform dose of ultrasonic energy to the treatment site. In other applications, it is desired to deliver greater amounts of ultrasonic energy or ultrasonic energy of a different frequency to different portions of the treatment site. The individual control of the ultrasound radiating members described above allows the ultrasound assembly to deliver the appropriate amount and quality of ultrasonic energy to the treatment site.

For example, piezoelectric transducers can be used to generate ultrasonic energy. Piezoelectric transducers produce ultrasonic energy when an electric voltage is applied to certain crystalline structures. The characteristics of the ultrasonic energy generated by a piezoelectric transducer is determined by the crystalline structure of the transducer, as well as by the frequency and voltage at which the transducer is driven.

As shown in FIG. 12, the isolation pod 200 includes circuitry for controlling the generation of ultrasonic energy. In one embodiment, an alternating current ("AC") signal is provided to the isolation pod 200 from an external source. In another embodiment, the AC signal is generated within the isolation pod 200 using circuitry such as a crystal oscillator. In one embodiment, the AC signal drives the ultrasound radiating members directly. In a modified embodiment, the isolation pod 200 includes additional circuitry to modify the AC signal before driving the ultrasound radiating members.

As discussed above, and as shown in FIG. 12, in certain embodiments the catheter further comprises temperature sensors. As illustrated, the current source applies a constant current bias across a silicon P-N diode junction. At a constant current bias, the voltage drop across a silicon P-N diode junction shows roughly a $-2$ mV $°$ C.$^{-1}$ temperature coefficient. The arrangement of temperature sensor diodes in the catheter together with the diode path selection switches and the reversible current source allows the isolation pod 200 to select a single diode from the set of twelve diodes for measuring the temperature. The remaining diodes are either switched out of the circuit or reverse biased. A pre-amplifier circuit amplifies the voltage drop across the diode and provides a signal to an analog to digital (A/D) converter.

Figure 19:
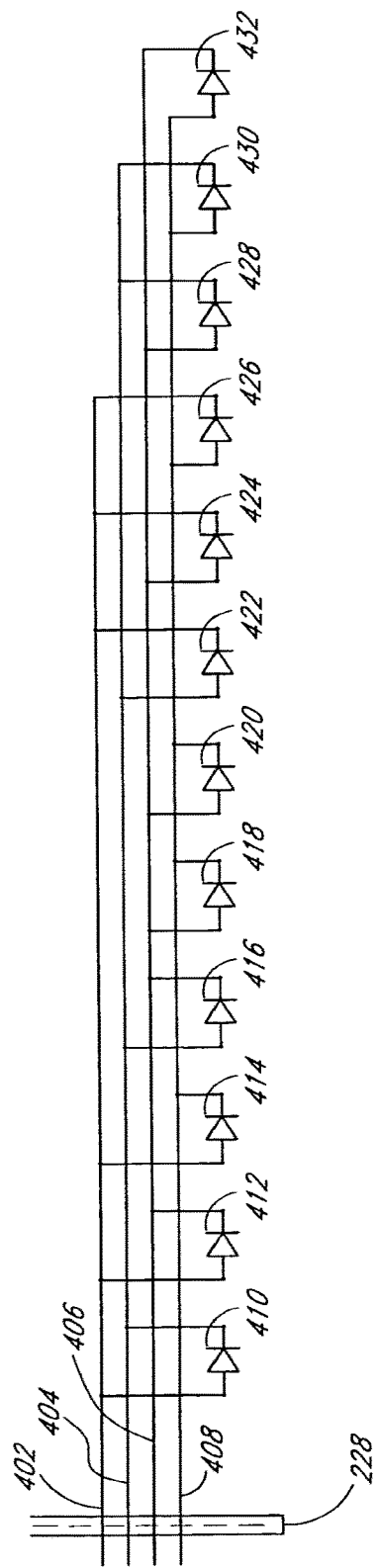
FIG. 19 illustrates the connection of temperature sensors within a catheter to an isolation pod.

FIG. 19 illustrates a diode arrangement within a catheter. In this embodiment, configuring a first set of switches in the (open, closed) setting, a second set of switches in the (closed, open) setting, and the remaining to sets of switches in the (open, open) setting results in one diode being forward biased and a second diode being reverse biased. The remaining diodes are left floating at one or both terminals. The direction of the current is controlled by a single-pull double-throw (SPDT) switch as illustrated in FIG. 12. The direction of the current determines which of the two non-floating diodes is forward biased.

Because there may be some variance in the diodes when used as temperatures sensors, one embodiment utilizes a calibration process. For example, calibration data may be included in the ID PROM 254. In modified embodiments, the diodes can be calibrated against an ambient temperature reading.

In other embodiments, the temperature sensors 20 monitor the temperature of the treatment site at which the catheter is operating. For example, in one embodiment a temperature sensor is placed near a ultrasound radiating member to measure the temperature of the tissue near the catheter. In other embodiments, a temperature sensor is positioned between two ultrasound radiating members to measure the average energy delivered by the ultrasound assembly.

Referring again to the isolation pod 200 illustrated in FIG. 12, power is provided through the power isolation transformer 276. Communications data can be modulated with the power signal. For example, the embodiment illustrated in FIG. 12 further comprises a modulator/demodulator ("modem") configured to transmit and receive signals modulated on the power signal. This allows a microcontroller 272 to communicate with the external control circuitry 100. In such embodiments, the external control circuitry 100 can effectively control the activation of ultrasound radiating members and diodes by sending commands to the microcontroller. Or, in modified embodiments, the microcontroller can execute control sequences from memory. The microcontroller preferably includes outputs to control the switches and other drivers within the isolation pod 200.

Still referring to FIG. 12, a PROM 254 contains information relating to a number of factors, including but not limited to the catheter length, the number of ultrasound radiating members, the center frequency at which each ultrasound radiating member should be run, the tuning parameters for the ultrasound radiating members, and the calibration factors for the temperature sensors. A catheter connector 230, illustrated in FIG. 20, and which will be described in detail below, provides connection between the wires in the isolation pod 200 and the wires in the cable 45. These wires carry electrical signals between the isolation pod 200 and the inner core 34 located within the catheter 10.

Figure 20:
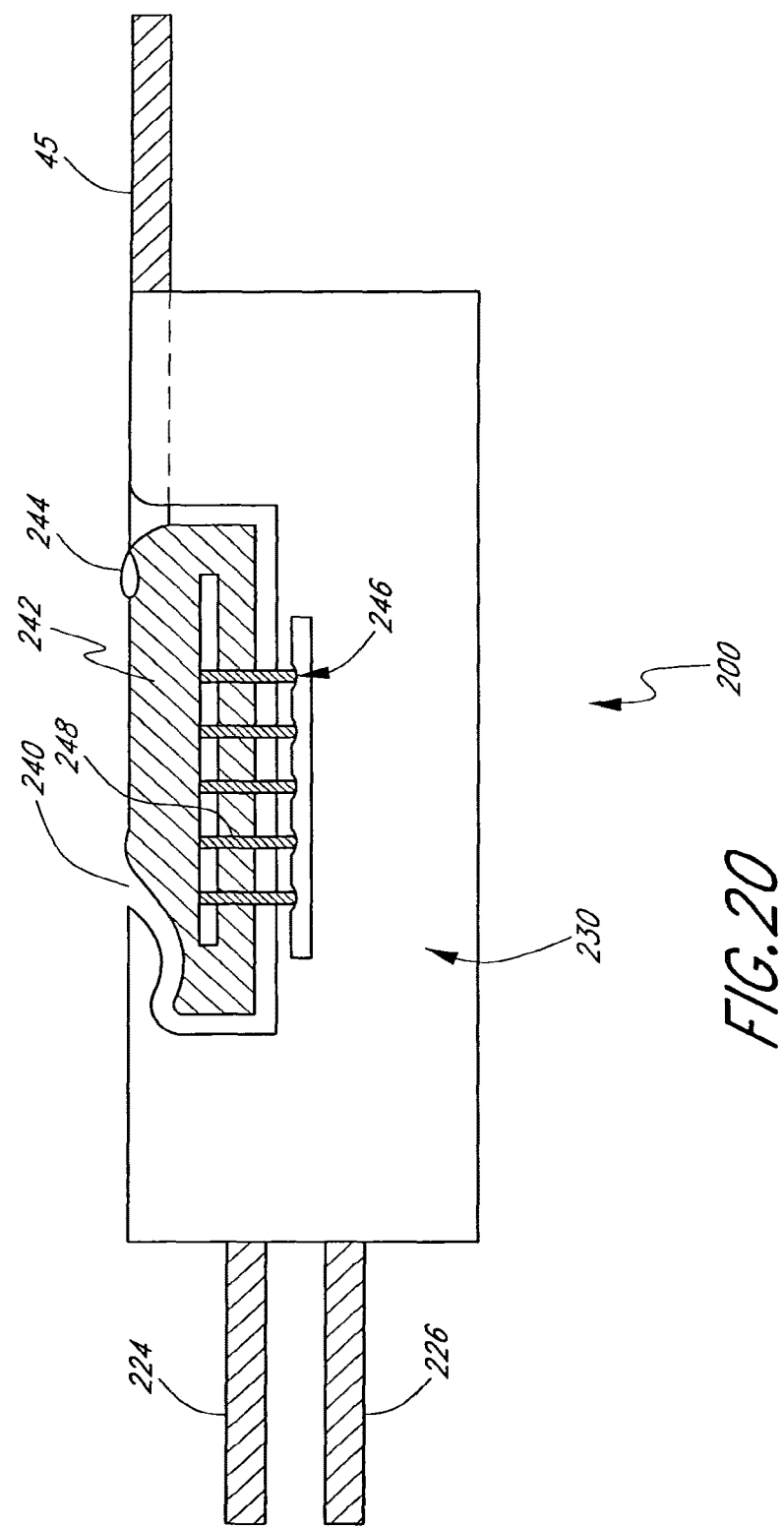
FIG. 20 is a cross-sectional view of a catheter connector.

As illustrated in FIG. 20, the connection between the isolation pod 200 and the catheter 10 generally comprises a catheter connector 230. The catheter connector 230 is preferably integral with the isolation pod 200, and generally comprises a customized slot 240 into which the cable 45 fits. One advantage of having the catheter connector 230 integral with the isolation pod 200 is the reduction in physical space and costs that are associated with using an additional cable and connection device outside the isolation pod 200. In the illustrated embodiment, a toe-catch arrangement assures a proper fit and assists in keeping the connecting end of the cable 45 within the customized slot. The catheter connector 230 preferably includes a latch 244 to secure the connecting end of the cable 45 within the customized slot 240.

Still referring to FIG. 20, the catheter connector 230 preferably comprises an array of gold spring contacts 246 which provide an electrical connection between the isolation pod 200 and the cable 45. The wire contacts at the connecting end of the cable are configured to be aligned with the gold spring contacts 246 of the connector 230. The catheter connector 230, the cable 45, and their respective components can be manufactured in accordance with any of the variety of techniques well known in the electrical interfacing and wiring fields.

In the embodiment illustrated in FIG. 12, a catheter houses the ultrasound radiating members and the temperature sensors. In such embodiments, the catheter is connected to the isolation pod 200 which houses the electronics capable of driving the ultrasound radiating members, as well as additional electronics capable of processing temperature signals received from the catheter. In one embodiment, the isolation pod 200 receives control signals from external circuitry 300, and transmits data back to the external circuitry using a data interface 252.

In another embodiment, all or part of the electronics for driving the ultrasound radiating members is housed within the backend hub 33. Similarly, all or part of the electronics for processing the temperature signals is can be housed within the backend hub 33 as well. However, because certain catheters described herein are intended to be disposable, the cost of the catheter can be reduced by minimizing the amount of electronics contained within the catheter. Additionally, reducing the amount of electronics contained within the catheter also reduces the catheter size. Thus, catheters configured to operate in narrow passages such as small vessels will also benefit from the reduction of electronics contained within the catheter. Therefore, in other embodiments, minimal electronics is incorporated within the catheter.

A user may connect multiple types of catheters to a single isolation pod 200. To identify the type of catheter connected to the isolation pod 200, the catheter preferably includes electronics containing an identifying code. The identifying code conveys information such as the type of catheter, the serial number of the catheter, the manufacturing location of the catheter, the date of manufacture, or other identifying information. In one embodiment, the circuitry for storing the identifying code is a PROM 254. Other types of memory such as flash memory or non-volatile random access memory ("RAM") can also serve to identify the catheter. Electronics such as switches, jumpers, diodes, or hard wired connections can also serve to identify the catheter. One of ordinary skill in the art will recognize that other circuits not disclosed herein will also provide identification of the catheter.

Information contained on the identification PROM 254 can include, for example, the length of the catheter, the length of the treatment zone, the number of ultrasound radiating members in the catheter, the ultrasound radiating member layout, the resonant frequency of the ultrasound radiating members, tuning information for the ultrasound radiating members, compensation and/or calibration data for the diodes, or patterns for driving the ultrasound radiating members.

As illustrated in FIG. 12, in one embodiment, temperature sensitive diodes 238 are used as sensors to measure a temperature near the catheter. In such embodiments, a pair of temperature sensitive diodes 238 is selectively enabled, and an output signal is provided to an analog to digital ("A/D") converter. Or, in modified embodiments, multiple pairs of diodes are activated with the output signals being provided to the A/D converter simultaneously. Other embodiments include a sensor to measure the ambient temperature, which is used, for example, to calibrate the temperature sensors. Additionally, the ambient temperature provides information as to whether the catheter and isolation pod are functioning properly.

Still referring to FIG. 12, the output of the A/D converter 270 is provided to a microcontroller 272 for analysis. The microcontroller 272 monitors the heat produced by the various ultrasound radiating members and/or the temperature of the tissue near the catheter, and uses such information to provide control signals to adjust characteristics such as signal strength or frequency of the driving signal provided to the individual ultrasound radiating members.

One of ordinary skill in the art will recognize that the various embodiments of the isolation pod described above, and illustrated in FIGS. 14 through 20, can be used with the catheter and various ultrasound radiating member and temperature sensor configurations illustrated in FIGS. 2 through 8. In addition, the various embodiments of the isolation pod described above, and illustrated in FIGS. 14 through 20, can also be used with other ultrasound radiating member and temperature sensor configurations not specifically described herein. For example, the isolation pod may also be used with an ultrasonic catheter that has only one ultrasound radiating member and/or is configured to fit within the small vessels of the body such as the small vessel catheters described in co-pending U.S. patent application, entitled "Small Vessel Ultrasound Catheter", filed on the same date as the present application.

While the foregoing detailed description has described several embodiments of the apparatus and methods of the present invention, it is to be understood that the above description is illustrative only and not limited of the disclosed invention. It will be appreciated that the specific dimensions of the various catheters and inner cores can differ from those described above, and that the methods described can be used within any biological conduit in a patient's body, while remaining within the scope of the present invention. Thus, the present invention is to be limited only by the claims that follow.

We claim:

1. An ultrasonic catheter comprising:
    a tubular body having a proximal end, a distal end and a treatment zone located between the distal end and the proximal end;
    a plurality of fluid delivery lumens defined within a wall of the tubular body and extending from the proximal end of the tubular body into the treatment zone;
    an inner core comprising at least one ultrasound radiating element, the at least one ultrasound radiating element being positioned within the treatment zone;
    a plurality of cooling fluid channels extending from a proximal end of the tubular body to the treatment zone, the plurality of cooling fluid channels being formed between an inner surface of the tubular body and an outer surface of the inner core, each cooling fluid channel being positioned generally radially between two fluid delivery lumens.

2. The ultrasonic catheter of claim 1, wherein the catheter includes three fluid delivery lumens.

3. The ultrasonic catheter of claim 1, wherein the catheter includes three cooling fluid channels.

4. The ultrasonic catheter of claim 1, wherein the three fluid delivery lumens spaced approximately 120 degrees radially apart from each other.

5. The ultrasonic catheter of claim 1 further including a control system comprising external circuitry and an isolation pod that is configured to be electrically connected to the inner core, the isolation pod being positioned between the tubular body and the control system and comprising an isolation barrier and circuitry for driving the ultrasound radiating element.

6. The ultrasonic catheter of claim 5, wherein the external circuitry provides a radio frequency signal to the isolation pod.

7. The ultrasonic catheter of claim 6, wherein the isolation pod includes a transformer for converting the radio frequency to a drive signal for driving the ultrasound radiating member.

8. The ultrasonic catheter of claim 5, wherein the isolation pod includes a transformer loop that is configured to measure leakage current through the tubular body.

9. The ultrasonic catheter of claim 5, wherein the isolation pod includes tuning circuitry that adjusts an input impedance based upon the activation of an ultrasound transducer.

10. The ultrasound catheter of claim 5, wherein the inner core comprises more than one ultrasound radiating elements.

11. The ultrasonic catheter of claim 5, wherein the ultrasonic catheter includes a memory device that stores information relating to the catheter.

\* \* \* \* \*

UNITED STATES PATENT AND TRADEMARK OFFICE
CERTIFICATE OF CORRECTION

| | | |
|---|---|---|
| PATENT NO. | : 10,080,878 B2 | Page 1 of 1 |
| APPLICATION NO. | : 15/207371 | |
| DATED | : September 25, 2018 | |
| INVENTOR(S) | : Richard R. Wilson | |

It is certified that error appears in the above-identified patent and that said Letters Patent is hereby corrected as shown below:

On the Title Page

Column 2 (Item (56)), Line 61, under Other Publications, change "Transactios" to --Transactions--.

In the Specification

Column 1, Line 12, change "8,167,832," to --8,167,831,--.

Column 6, Line 15, change "Uronkinase," to --Urokinase,--.

Column 7, Line 12, change "may by" to --may be--.

Column 13, Lines 13-14, change "thermalchromic" to --thermochromic--.

Column 18, Line 34, change "In this" to --In--.

Column 20, Line 60, change "to" to --two--.

In the Claims

Column 24, Line 35, in Claim 10, change "ultrasound" to --ultrasonic--.

Signed and Sealed this
Nineteenth Day of March, 2019

Andrei Iancu
*Director of the United States Patent and Trademark Office*